United States Patent [19]

Jarvik

[11] Patent Number: 5,092,879
[45] Date of Patent: Mar. 3, 1992

[54] INTRAVENTRICULAR ARTIFICIAL HEARTS AND METHODS OF THEIR SURGICAL IMPLANTATION AND USE

[76] Inventor: Robert K. Jarvik, 124 W. 60th St., New York, N.Y. 10023

[21] Appl. No.: 489,773

[22] Filed: Mar. 5, 1990

Related U.S. Application Data

[63] Continuation of Ser. No. 156,896, Feb. 17, 1988, abandoned.

[51] Int. Cl.$^5$ .............................................. A61M 1/10
[52] U.S. Cl. .......................................... 623/3; 600/16
[58] Field of Search ........................... 600/16–18; 623/3, 2; 417/423.12, 423.7, 423.1; 415/900

[56] References Cited

U.S. PATENT DOCUMENTS

| | | | |
|---|---|---|---|
| 2,635,547 | 4/1953 | Cataldo | 417/423.12 |
| 2,824,520 | 2/1958 | Bartels | 417/423.7 |
| 3,425,064 | 2/1969 | Carnevale et al. | 3/1 |
| 3,478,695 | 11/1969 | Goranson et al. | 103/152 |
| 3,491,377 | 1/1970 | Bolie | 3/1 |
| 3,505,987 | 4/1970 | Heilman | 128/1 |
| 3,512,183 | 5/1970 | Sharp et al. | 3/1 |
| 3,513,486 | 5/1970 | DeBennetot et al. | 3/1 |
| 3,518,702 | 7/1970 | Russa | 3/1 |
| 3,526,005 | 9/1970 | Bokros et al. | 3/1 |
| 3,550,162 | 12/1970 | Huffman et al. | 3/1 |
| 3,562,352 | 2/1971 | Nyilas | 260/824 |
| 3,608,088 | 9/1971 | Dorman | 623/3 |
| 3,641,591 | 2/1972 | Keiff | 3/1 |
| 3,647,324 | 3/1972 | Rafferty | 623/3 |
| 3,656,873 | 4/1972 | Schiff | 417/395 |
| 3,668,708 | 6/1972 | Tindal | 3/1 |
| 3,685,059 | 8/1972 | Bokros et al. | 3/1 |
| 3,733,616 | 5/1973 | Willis, Jr. | 3/1 |
| 3,911,898 | 10/1975 | Leachman, Jr. | 128/1 D |
| 3,975,117 | 8/1976 | Carter | 417/423.12 |
| 3,995,617 | 12/1976 | Watkins et al. | 600/16 |

(List continued on next page.)

FOREIGN PATENT DOCUMENTS

| | | | |
|---|---|---|---|
| 0324669 | 7/1989 | European Pat. Off. | 623/3 |
| 2233293 | 1/1973 | Fed. Rep. of Germany | 600/16 |
| 1503906 | 12/1967 | France | 623/3 |
| 1514319 | 2/1968 | France | 623/3 |
| 2156443 | 10/1985 | United Kingdom | 623/3 |
| 85/01432 | 4/1985 | World Int. Prop. O. | 600/16 |

OTHER PUBLICATIONS

"An Artificial Heart that Doesn't Dent", JAMA, 2-1-8-1974, vol. 227, pp. 735-736.
Bregman, et al., "Left Ventricular and Unidirectional Intra-aortic Balloon Pumping", The Journal of Thoracic and Cardiovascular Surgery, vol. 68, No. 5, Nov. 1974, pp. 677-686.
Donald, et al., "Circulatory Support by a Left Ventricular Balloon Pump", Cardiovascular Surgery 1970, pp. I-96 to I-100.
Ross, et al., "The Architecture of the Heart in Systole and Diastole: Technique of Rapid Fixation and Analysis of Left Ventricular Geometry", Circulation Research, vol. XXI, Oct. 1967, pp. 409-421.
Dodge, et al., "Usefulness and Limitations of Radiographic Methods for Determining Left Ventricular Volume", The American Journal of Cardiology, vol. 18, Jul. 1966, pp. 10-24.
H. Arvidsson, "Angiocardiographic Determination of Left Ventricular Volume", Acta Radiologica, vol. 56, Nov. 1961, pp. 321-339.

*Primary Examiner*—Randall L. Green
*Assistant Examiner*—David H. Willse
*Attorney, Agent, or Firm*—Edgar H. Haug; John M. Kilcoyne

[57] ABSTRACT

A method of treating heart failure is disclosed in which, without removing the damaged heart, implantation of prosthetic blood-pumping means within the natural heart sustains its function. The invention includes electrically-powered positive displacement pumps, muscle-powered pumps, and electrically-powered rotary hydrodynamic pumps sufficiently miniaturized and adopted to function within the heart. The invention also includes surgical connectors and surgical methods that permit intraventricular artificial hearts to be effectively applied.

8 Claims, 15 Drawing Sheets

U.S. PATENT DOCUMENTS

| | | | |
|---|---|---|---|
| 4,014,318 | 3/1977 | Dockum et al. | 128/1 D |
| 4,015,590 | 4/1977 | Normann | 128/1 D |
| 4,034,742 | 7/1977 | Thoma | 128/1 D |
| 4,041,931 | 8/1977 | Elliott et al. | 128/1 R |
| 4,051,840 | 10/1977 | Kantrowitz et al. | 128/1 D |
| 4,078,267 | 3/1978 | Cieszynski | 3/1.7 |
| 4,080,958 | 3/1978 | Bregman et al. | 128/1 D |
| 4,102,610 | 7/1978 | Taboada | 623/3 |
| 4,131,604 | 12/1978 | Szycher | 528/79 |
| 4,134,712 | 1/1979 | Kemmner | 417/423.12 |
| 4,135,253 | 1/1979 | Reich | 623/3 |
| 4,135,494 | 1/1979 | Stoner et al. | 128/1 R |
| 4,143,425 | 3/1979 | Runge | 3/1.7 |
| 4,143,661 | 3/1979 | LaForge et al. | 128/419 R |
| 4,152,786 | 5/1979 | Clark et al. | 3/1.7 |
| 4,166,466 | 9/1979 | Jarvik | 128/325 |
| 4,173,689 | 11/1979 | Lyman et al. | 521/64 |
| 4,173,796 | 11/1979 | Jarvik | 623/3 |
| 4,187,852 | 2/1980 | Urry et al. | 128/334 R |
| 4,240,409 | 12/1980 | Robinson et al. | 128/1 D |
| 4,302,854 | 12/1981 | Runge | 623/3 |
| 4,382,199 | 5/1983 | Isaacson | 623/3 |
| 4,453,537 | 6/1984 | Spitzer | 128/1 D |
| 4,507,048 | 3/1985 | Belenger | 415/900 |
| 4,573,997 | 3/1986 | Wisman et al. | 623/3 |
| 4,600,405 | 7/1986 | Zibelin | 623/3 |
| 4,625,712 | 12/1986 | Wampler | 623/3 |
| 4,652,263 | 3/1987 | Herweck et al. | 623/1 |
| 4,688,998 | 8/1987 | Olsen | 623/3 |
| 4,704,121 | 11/1987 | Moise | 623/3 |
| 4,756,302 | 7/1988 | Portner | 623/3 |
| 4,771,765 | 9/1988 | Choy et al. | 604/101 X |
| 4,817,586 | 4/1989 | Wampler | 600/16 |
| 4,919,661 | 8/1990 | Gibney | 623/3 |

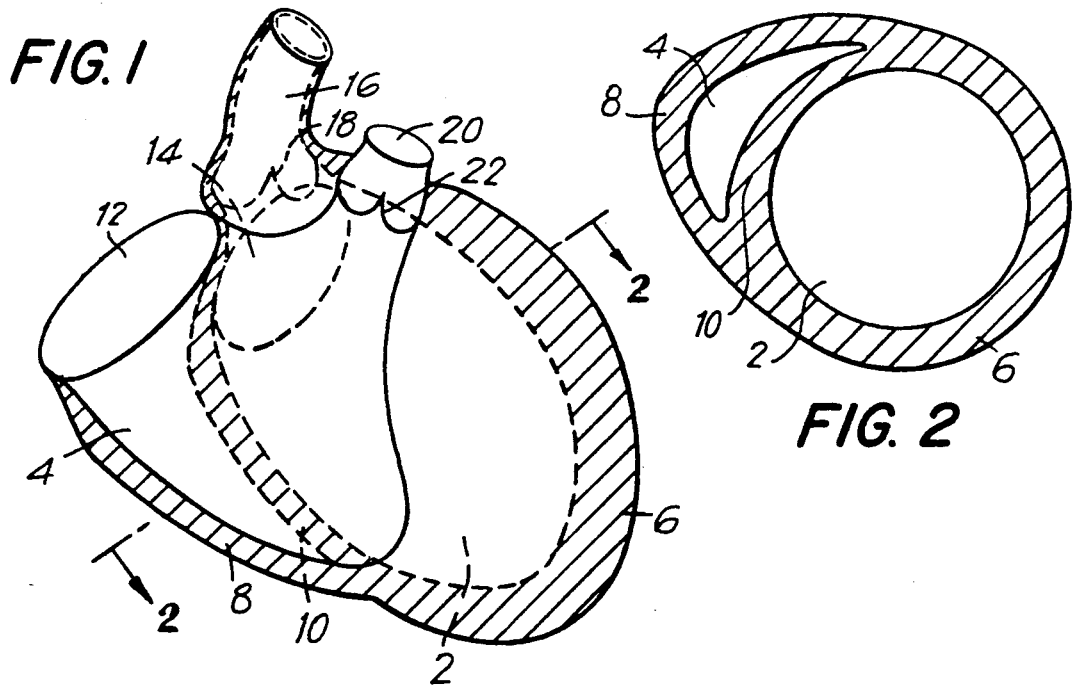
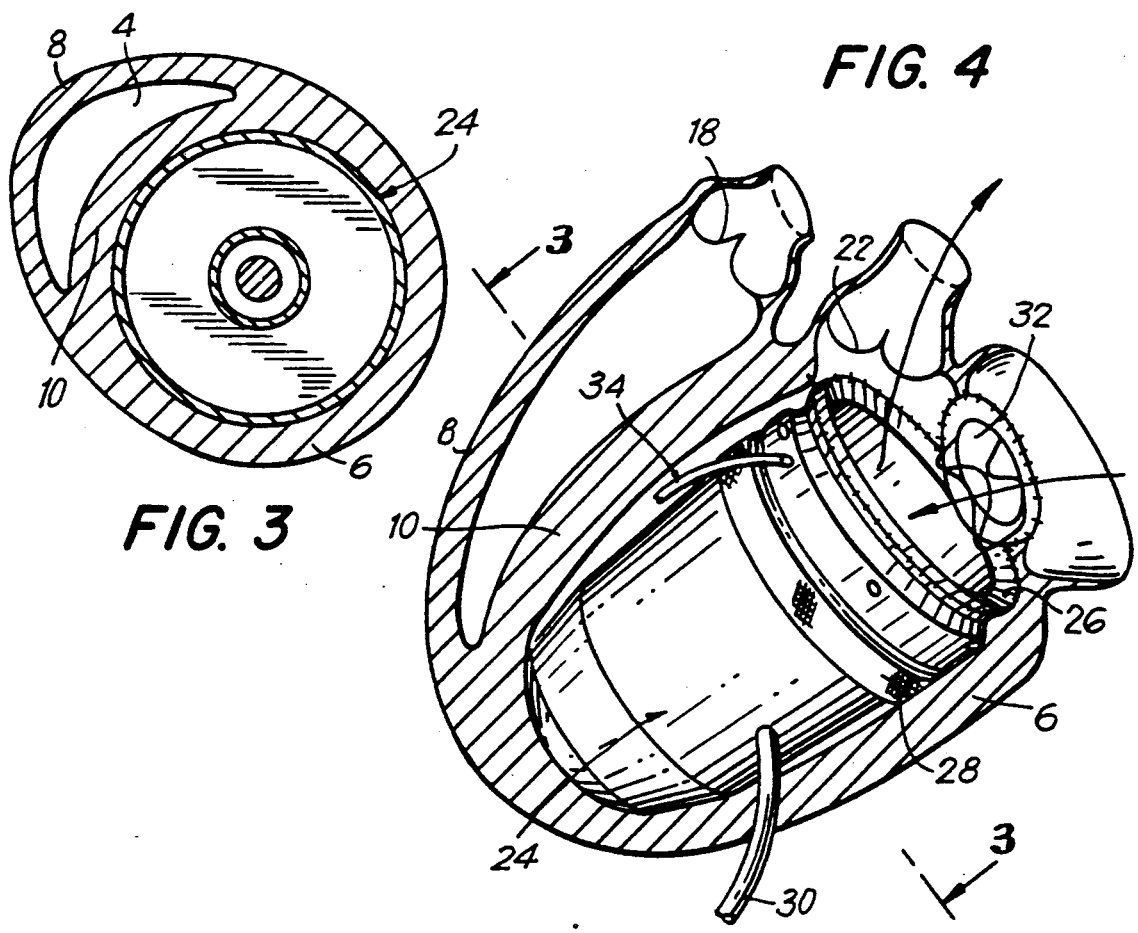

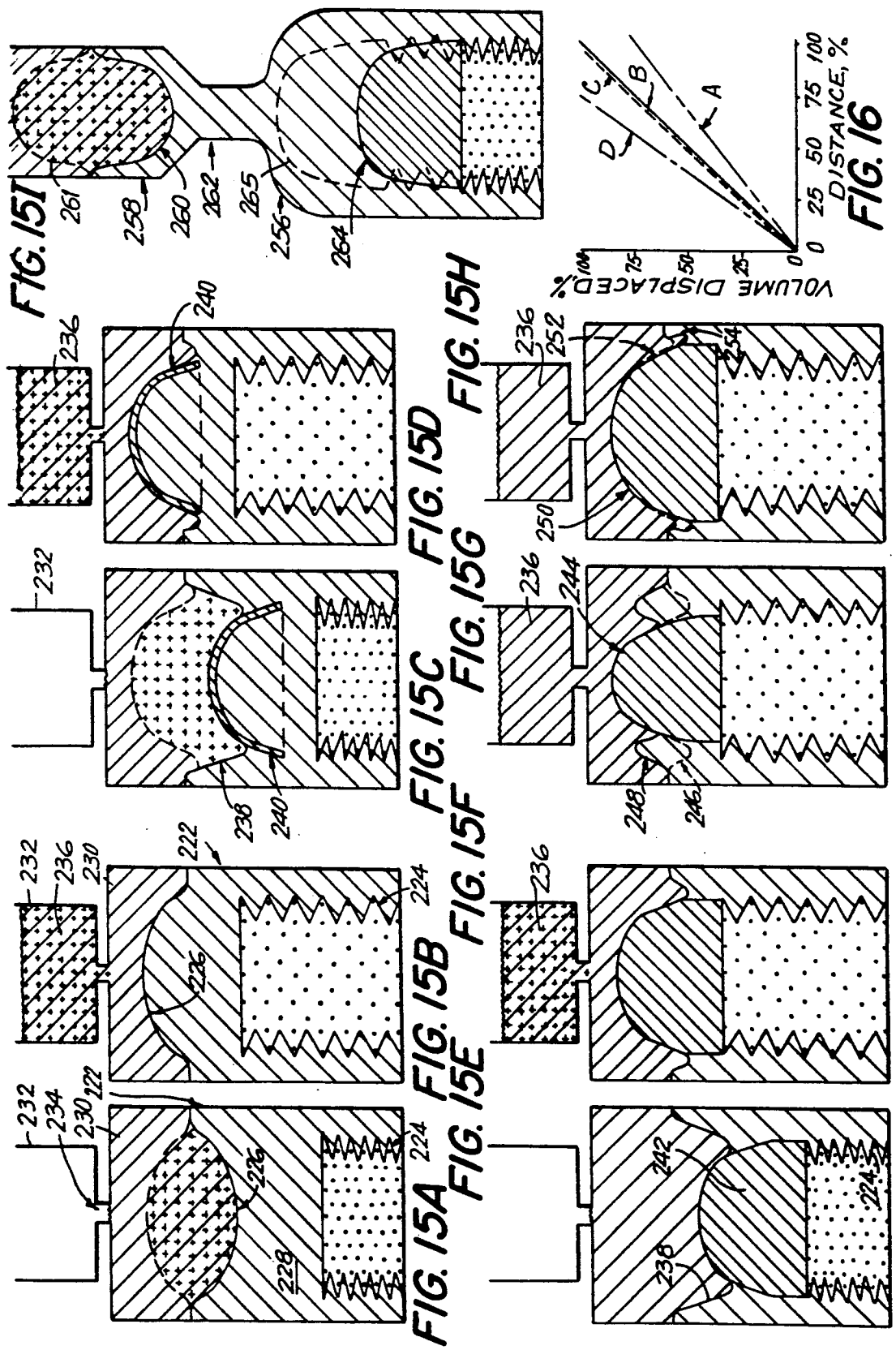

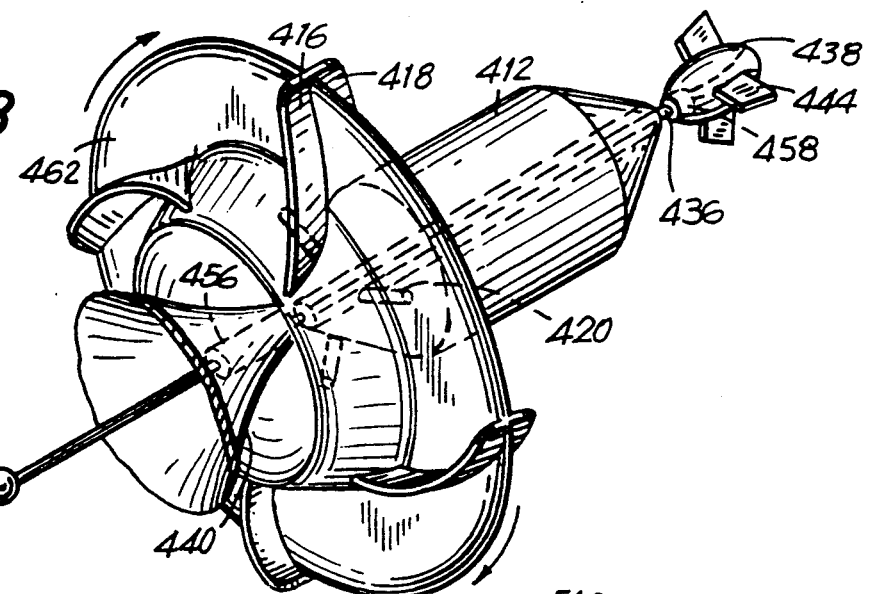
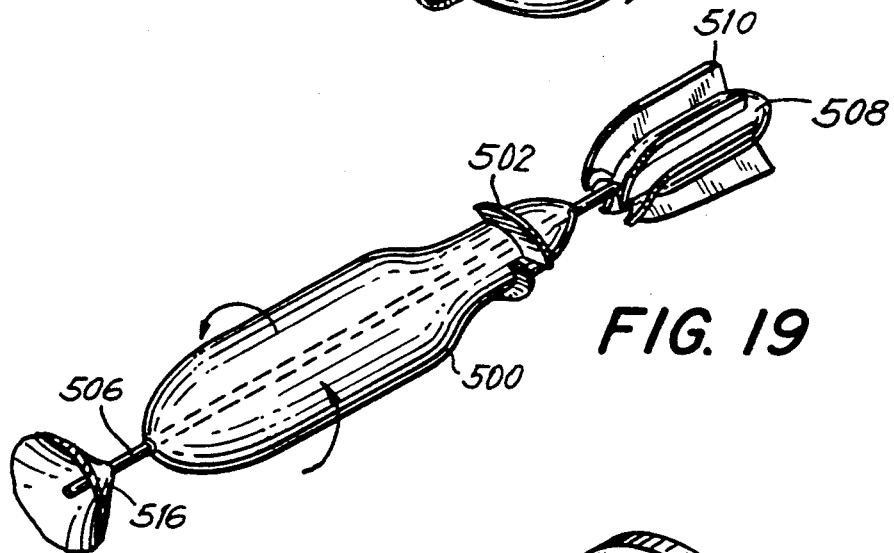
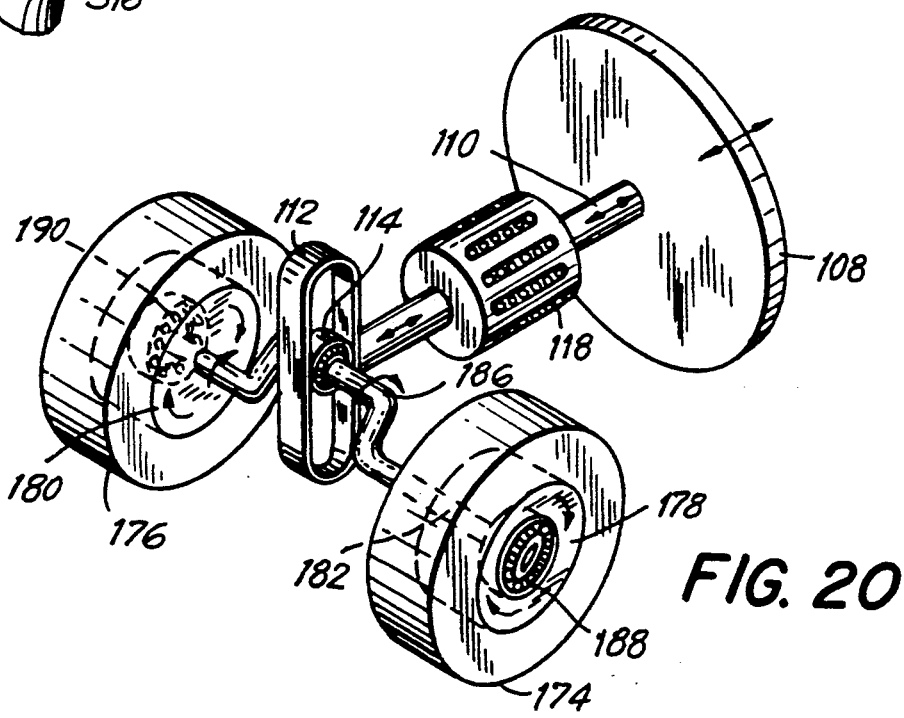

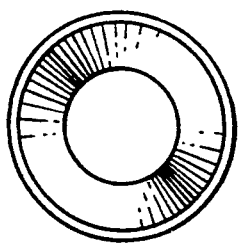
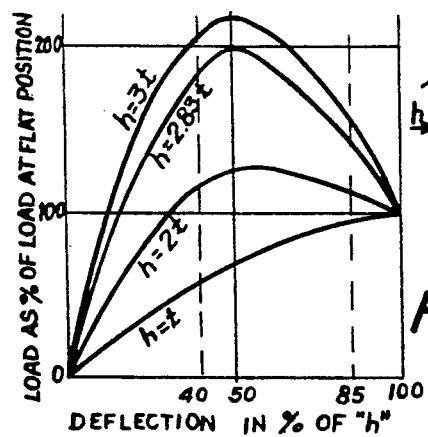
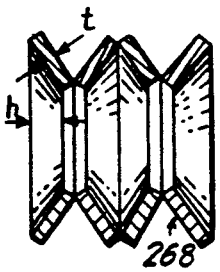
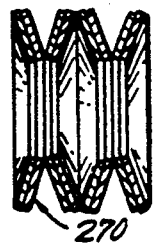
FIG. 21A    FIG. 21B    FIG. 21C    FIG. 21D
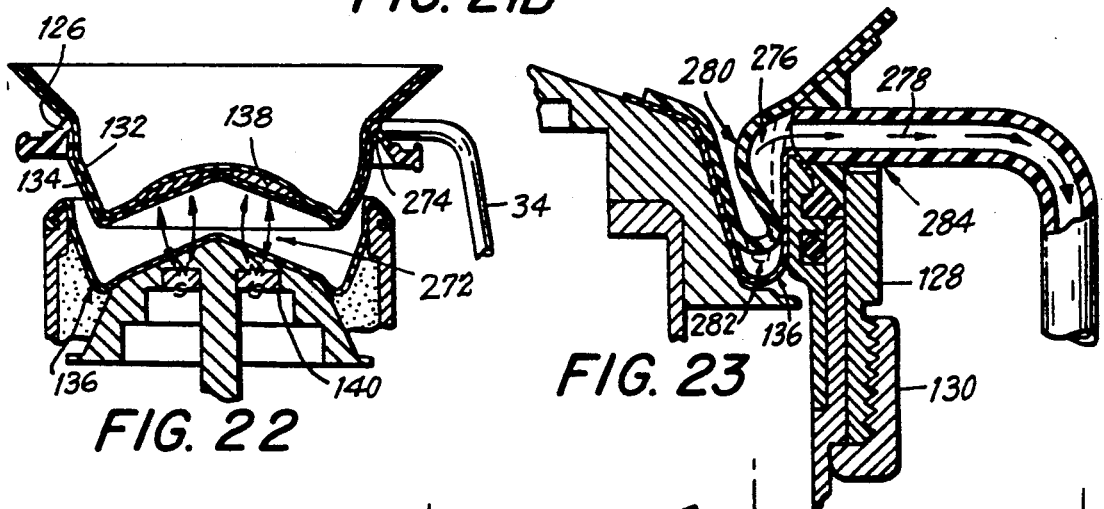
FIG. 22    FIG. 23
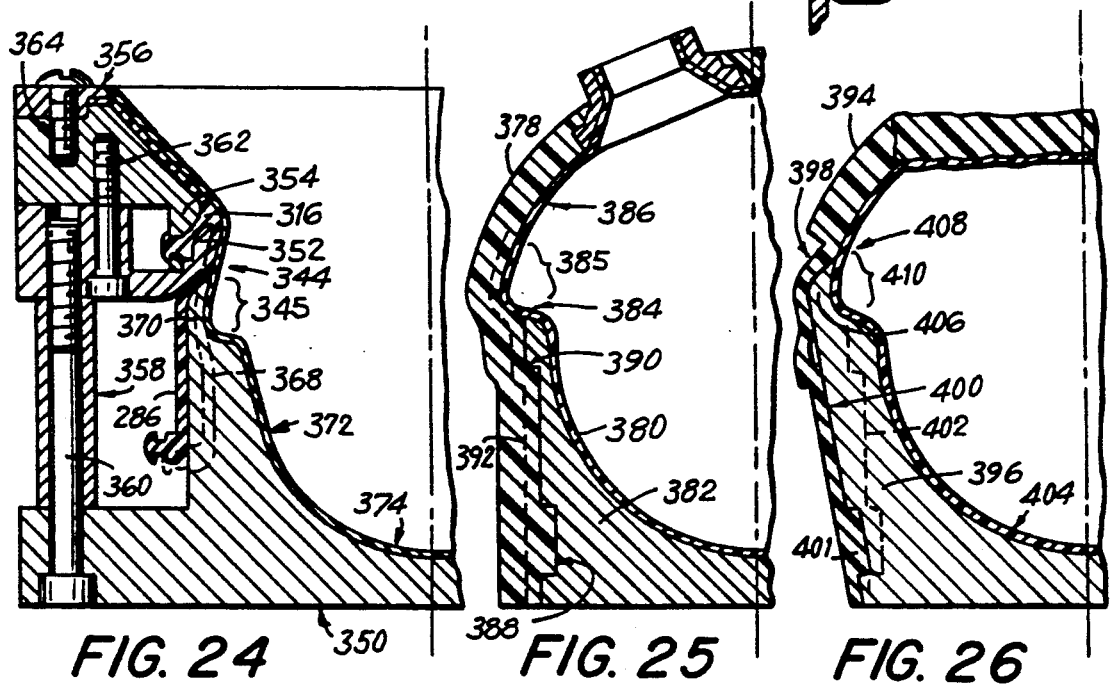
FIG. 24    FIG. 25    FIG. 26

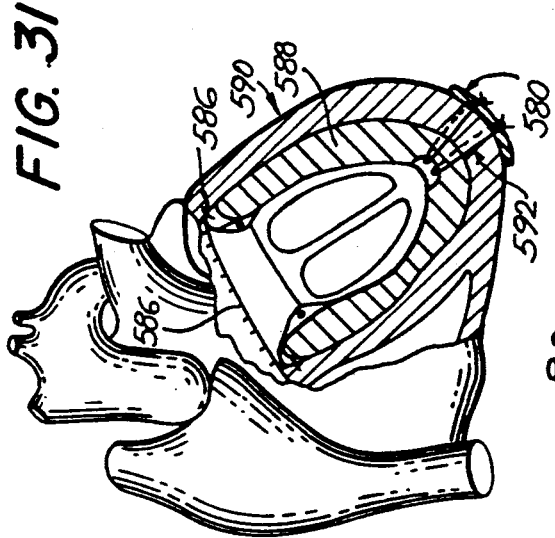
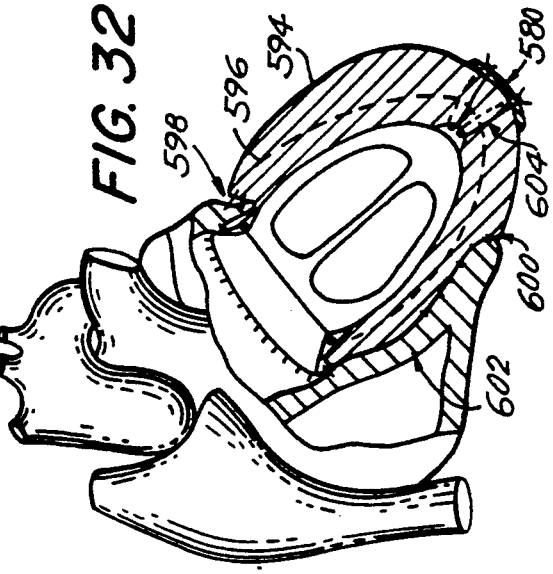
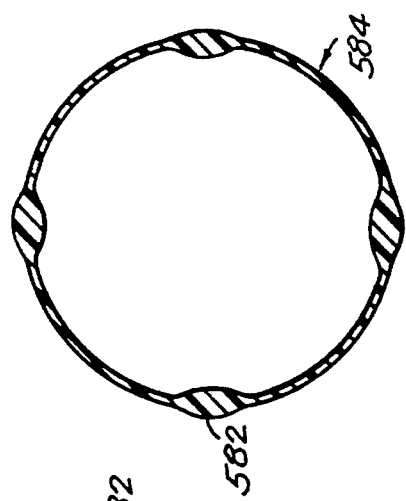
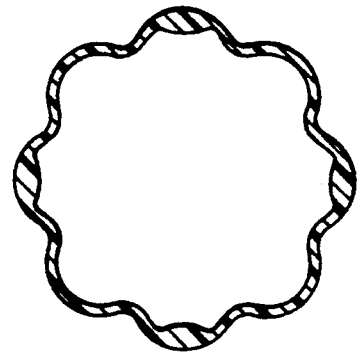
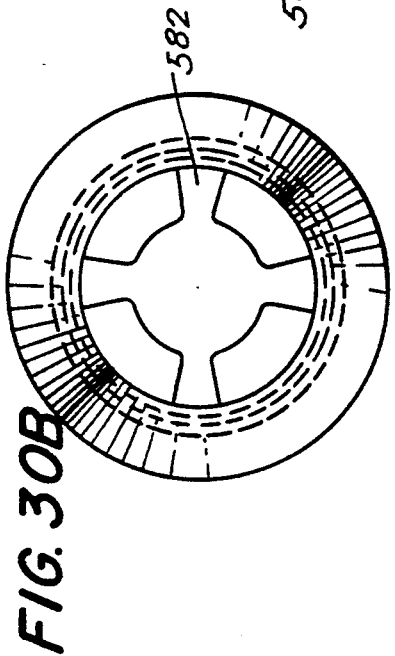
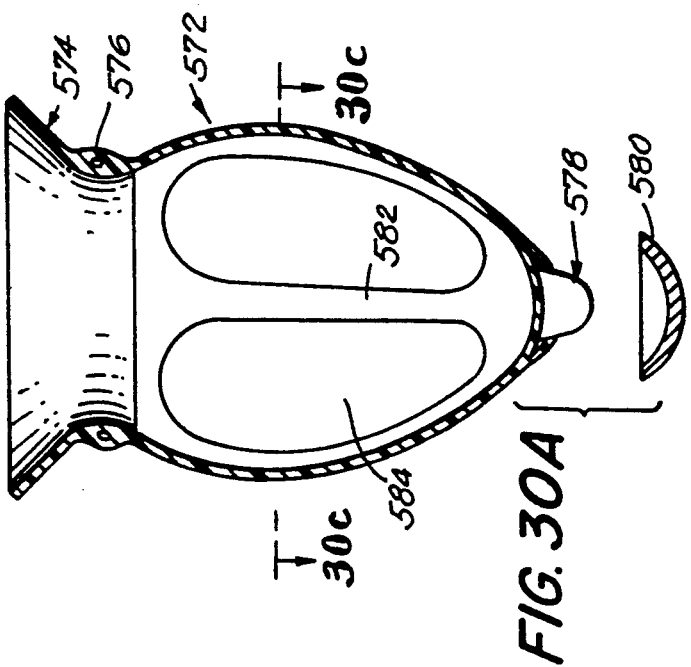

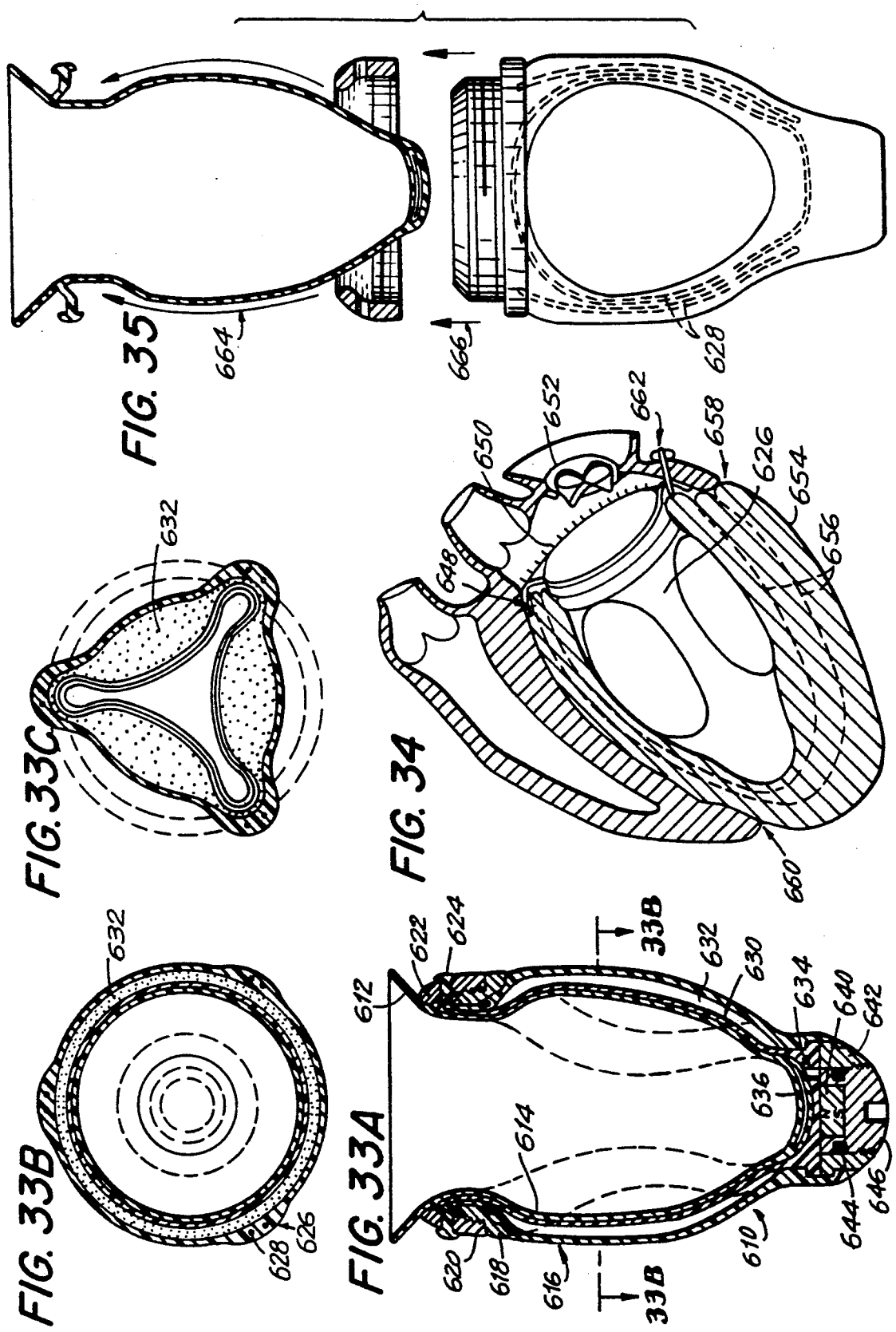

INTRAVENTRICULAR ARTIFICIAL HEARTS AND METHODS OF THEIR SURGICAL IMPLANTATION AND USE

This application is a continuation of application Ser. No. 156,896, filed Feb. 17, 1988, now abandoned.

BACKGROUND

The widespread success of cardiac transplantation has definitively proven that replacement of the irreparably damaged heart can sustain patients in good health for many years. The use of a transplanted second heart in the "Piggyback" position has further illustrated that functional support of the badly damaged heart is also highly effective. In 1986, more than 1300 patients received heart transplants in the United States but many thousands who could have been saved with heart transplants died because there were not enough available donor organs. Studies indicate that more than 10,000 patients per year would be candidates for heart transplantation if enough organ donors were available, and many more would be candidates for permanent artificial hearts and cardiac assist devices. Some estimates place the numbers of patients per year who could be saved with permanent artificial hearts between 17,000 to 80,000.

The JARVIK 7 ®[1] total artificial heart is the only permanent artificial heart which has been used in humans through 1987. The average survival of the five patients so treated was in excess of 9 months, with the longest patient surviving nearly two years (620 days). These patients experienced many complications associated with the early use of a new technology; however, the feasibility of long-term survival was established.

[1] JARVIK 7 ® is a registered trademark of Symbion, Incorporated, Salt Lake City, UT.

The JARVIK 7 ® heart has been used much more extensively as a temporary bridge to transplant to permit patients to survive long enough for a donor heart to be obtained. More than 80 patients were implanted with the JARVIK 7 ® heart as a bridge during 1985, 1986, and 1987. The procedure has been done at twenty medical centers in five countries with greater than 75% success, defined as the ability to sustain the patient long enough to receive a donor organ. A high percentage of these patients have survived long term, and many are back to work full time.

Thus, it has clearly been demonstrated that artificial hearts can be effectively used on a widespread basis, and that long-term survival can be obtained. However, to date, no artificial heart system has been developed which is truly practical for widespread application in thousands of patients. The problems associated with present devices involve the inability to provide a high quality of life with high mobility, adequate cardiac function for moderate exercise, and freedom from complications, including blood damage, blood clotting, and infection. Additionally, present systems are relatively cumbersome and require a very extensive level of follow-up care, including medical management of the patient and work with the artificial heart drive equipment.

Each of the numerous artificial hearts that has been patented or disclosed in the literature has attempted to solve one or more problems recognized as important for successful function of artificial hearts. Some attempts have been made to develop artificial heart systems which provide a sufficiently acceptable solution to all crucial functional problems and could, therefore, be truly practical. The reversing electro-hydraulic artificial heart disclosed in my U.S. Pat. No. 4,173,796 was one attempt at such a system. Nuclear-powered artificial hearts developed by the Atomic Energy Commission and The National Institutes of Health, as well as electrically-powered left ventricular assist systems, such as the Thermetics System and the Novacor System, developed with N. I. H. support, have been other attempts. However, all these devices have suffered from problems related to system complexity, large size and weight, or difficulty in control modes and certain fundamental characteristics such as the presence of connectors and crevices within the devices where blood clots can form. No truly seamless electrically- or pneumatically-powered artificial heart system has been disclosed in the prior art.

The problem of thrombus formation and the potential for thromboembolism and stroke is not related only to the existence of seams and crevices within the artificial heart itself. It is also related to the materials of which the heart is fabricated and to the artificial heart valves used. These factors dictate the need for anticoagulant drugs which are undesirable although necessary with devices of the type presently used. Prosthetic heart valves may be categorized generally into mechanical and tissue valves. The mechanical valves generally require anticoagulation, and the tissue valves generally do not. Efforts to incorporate tissue valves into artificial hearts have met with varying degrees of success. As these valves are obtained from animals, they are of irregular shape and are difficult to mount within the artificial heart. However, they are highly efficient and function well at high heart rates. The mechanical valves, in general, are more easily mounted into artificial hearts but require anti-coagulation, may cause significant blood damage under certain pumping conditions, and may be the source of the greatest noise within the artificial heart. In some cases, surgical methods have been developed to preserve the natural outflow valves of the patient's heart, which reduces the number of prosthetic valves needed, reduces the risk of blood clots, and also reduces the cost.

Data from the patients sustained long term with the JARVIK 7 ® artificial heart indicates that the heart valves (Medtronic-Hall valves) were a major source of blood damage if the heart drive system was set to a high dp/dt value. They were a likely cause of damage to white blood cells and possibly affected the body's immune defenses. The valves were definite sites for thrombus formation (both on the valve stents and in the crevices where they are mounted to tne heart), and were formation of pannus (scar tissue overgrowth) in long-term cases. Selection and appropriate use of prosthetic heart valves with artificial heart systems can determine success or failure of the entire system.

Infection with permanent artificial hearts is another extremely important problem which is directly related to the design of the device and the follow-up care the patient receives. Pneumatically-powered artificial hearts having relatively large air tubes penetrating the skin carry a high risk of infection when used for periods in excess of one month. The percutaneous lead where the tubes penetrate the skin requires special cleansing and hygiene and is certainly a site where bacteria may enter. Although some successful percutaneous lead systems have been developed capable of permitting electric wires to be passed through the skin without infection for periods as long as ten years, no effective systems for preventing infection with large diameter tubes have been developed to date.

There is little doubt that infection is related not only to a direct mechanism of entry of the infecting organisms into the body but also is related to the presence of prosthetic materials within the body and the body's defense mechanisms in the vicinity of these prosthetic materials. For example, prosthetic heart valves may become infected following dental work when bacteria entering the blood stream near the teeth are carried to the heart and infect the artificial valves. Most artificial heart systems are complex devices with a large surface area of foreign materials within the body. When these foreign materials are placed in certain areas susceptible to infection, the artificial heart may become infected. Surgical procedures which do not prevent all bleeding at the time of closing the chest may leave blood clots around the outside of the artificial heart and within the chest cavity that can serve as a source of nutrients to infecting bacteria.

In order to present the lowest risk of infection, artificial heart systems should:

(1) Cause no functional derangements in the immune system via the interaction of mechanical damage to the white blood cells or via other mechanisms.

(2) Permit surgical implantation with minimal bleeding.

(3) Present the minimal surface area of artificial materials to the bloodstream and occupy a minimum volume within the body without excessive surface area.

(4) Be anatomically adapted to fit within the body without causing pressure necrosis of the tissues.

(5) Heal into the body tissues well with close proximity of vascularized tissues in the vicinity of the surface of the artificial heart.

(6) Require no skin penetration unless such a system is a completely effective barrier against the entrance of bacteria. To meet the above criteria, the optimum artificial heart should be capable of implantation within the natural pericardial sac and thus should be as lightweight and compact as possible.

Approximately 80% of the hemodynamic work of the heart is performed by the left ventricle. Furthermore, disease of the right ventricle is far less common than disease of the left. For these and other reasons, many devices have been developed to assist the left ventricle while relying on the function of the natural right ventricle. Some cases have been reported in the literature of patients treated with left ventricular assist devices where there was no right ventricular function, and the patients survived, but in many cases with temporary assist, left ventricular support only is insufficient, and patients may die from right heart failure if no right ventricular support is provided. However, some surgical procedures have been developed to permit long survival in patients with congenital heart malformations where they essentially have no right ventricular function. Blood entering the right atrium is shunted directly into the pulmonary artery, and patients survive long term with no right ventricular pumping. Most left ventricular assist systems designed for permanent implantation have attempted to augment the pumping capability of the left ventricle and not replace it entirely. This has caused a number of significant constraints on the design of the systems and has often complicated control, requiring synchronization with the natural heart.

Frazier et al. (*Journal of Heart Transplantation*. Volume 5, Number 4, July/August 1986) have reported a method of replacing the left ventricle with an artificial ventricle while leaving the natural right ventricle in place. In this method, the left ventricular muscle is cut away from the heart, leaving the intraventricular septum in place. Thereafter, the artificial heart is connected to the atrium and aorta. The artificial ventricles used include two prosthetic heart valves and, with the exception of leaving the natural right ventricle in place, the surgical implantation technique is very similar to the techniques widely used to implant the left ventricle in the case of total artificial heart surgery. However, the concept of retaining right heart function and substituting an artificial ventricle for the natural ventricle on the left side has merit. Among the disadvantages of Frazier's method are the lack of mechanical support for the septum which distorts the natural anatomic relationship of the right heart thereby reducing its pumping efficiency, and disruption of the blood supply to the heart muscle which reduces its effectiveness.

Some efforts have been made to replace the function of the left myocardium including the use of mechanical devices implanted in the left ventricular muscle wall or balloons implanted within the cavity of the left ventricle or in the left ventricular muscle wall. One such device is the prosthetic myocardium developed by Dr. Adrian Kantrowitz. A disadvantage of a balloon placed in the left ventricle is that it interferes with the chordae tendineae of the mitral valve. If the natural ventricular muscle is weak, the heart may dilate and effectively act like a large ventricular aneurism, causing a great deal of compliance loss, which reduces the efficiency of the pumping function of the balloon. In effect, air is pumped into the balloon to displace blood by blowing the balloon up, the wall of the ventricle bulges to accommodate the change in volume, and the blood is not actually ejected out of the ventricle through the aortic valve. Thus, balloons in the left ventricle have limited effectiveness. Additionally, a prosthetic myocardium of the type developed by Dr. Kantrowitz can suffer from similar significant compliance losses if the natural tissues of the left ventricle are severely diseased or replaced by scar tissue.

The present invention places specially-designed blood pumps within the natural left ventricular cavity and a prosthetic valve, preferably a tissue valve, is implanted in the natural heart to replace the mitral valve using surgical techniques similar to conventional valve replacement. The patient's aortic valve may be preserved in some individuals or may also be replaced with a prosthetic valve. The blood pumps are very compact in order to fit within the cavity of the natural left ventricle. Pulsatile pumps operating at relatively high heart rates with a relatively small stroke volume are utilized. Rotary hydrodynamic blood pumps may also be utilized, in which case both the mitral and the aortic valves are excised. The artificial heart is surrounded by the natural left ventricular tissues, which remain within the pericardium. The natural coronary artery system is not disrupted, and therefore blood continues to flow to the natural myocardial tissues, which continue to beat. Right heart function is therefore preserved, and the septal geometry is relatively normal. The myocardial tissues which surround the artificial intraventricular blood pump provide a vascular supply to the outside of the artificial ventricle, permitting tissue ingrowth and a stable junction, which is protected from infection by the body's defense mechanisms provided via the vascular supply. The surface area of the blood-contacting membranes is minimized and can be made entirely seamless if the natural tissues of the heart are utilized to support the prosthetic heart valves that are not part of the artificial heart itself.

Table 1 compares heart transplants with ten types of permanent circulatory support systems. These general categories encompass most, but not all, of the possible permanent circulatory support systems. In each category, either left ventricular or biventricular systems are possible, and they are considered to be generally similar. The various systems are compared according to their availability, hemodynamic function, risk of thrombus, system complexity and reliability, infection or rejection risk, quality of life, and cost. The systems have been subjectively scored on a scale from 0 to 4, in the experience and judgment of the inventor, Dr. Jarvik, recognizing that somewhat different scores might be assigned by other experts in the field. These scores are based on reasonable expectations for the optimized devices of each category following major research and developments efforts. Heart transplant, nuclear-powered artificial hearts, intrathoracic electrical artificial hearts both transcutaneously and percutaneously powered, and intrathoracic pneumatic artificial hearts have all been extensively studied and reported in the literature. The scores assigned to the intraventricular designs of the present invention represent the realistic potential in the judgment of the inventor. This numerical comparison is given to emphasize areas of strengths and weaknesses in the varying existing designs. For any permanent circulatory support system to succeed, it must be acceptable in all of the mentioned categories. A score of 0, which represents the identification of an unacceptable weak point in the system, implies that the system will not be viable under present medical and socio-economic conditions. For example, the risk of infection for the pneumatic intrathoracic artificial hearts, which have large tubes penetrating the skin, has been assessed as unacceptable. Although patients' lives may be sustained for more than a year with such devices, ultimately the great majority of these hearts are expected to become infected and cause the deaths of the patients. It is not impossible that effective percutaneous infection barriers for large tubes could be developed, but at the present time, this appears unlikely.

A review of the comparative assessments given in table 1 shows that intraventricular artificial hearts may have the potential to surpass the performance of heart transplants and certainly have the potential to be far superior to present-day pneumatic and nuclear-powered artificial hearts. Intrathoracic transcutaneously-powered electric artificial hearts and intrathoracic muscle-powered devices also show reasonable potential for practical long-term success.

The preferred embodiment is electrically-powered, although intraventricular artificial hearts may be powered by many methods including electro-hydraulic and electro-magnetic actuators.

TABLE 1

| | | PERMANENT CIRCULATORY SUPPORT SYSTEMS | | | | | | |
|---|---|---|---|---|---|---|---|---|
| | | AVAILABILITY | HEMODYNAMIC FUNCTION | THROMBUS RISK | SYSTEM RELIABILITY | INFECTION/ REJECTION | QUALITY OF LIFE* | COST | TOTAL |
| ALL COMPONENTS IMPLANTED INTERNALLY WITHIN PERICARDIUM | | | | | | | | | |
| I | HEART TRANSPLANT | 1 | 4 | 4 | 4 | 3 | 4 | 2 | 22 |
| II | INTRAVENTRICULAR MUSCLE POWERED | 3 | 2 | 4 | 3 | 4 | 3 | 2 | 21 |
| WITHIN CHEST, ABDOMEN, ETC. | | | | | | | | | |
| III | INTRATHORACIC BLOOD PUMP WITH INTRATHORACIC MUSCLE POWER | 3 | 2 | 3 | 3 | 4 | 3 | 2 | 20 |
| IV | INTRAVENTRICULAR BLOOD PUMP WITH INTRATHORACIC MUSCLE POWER | 3 | 2 | 4 | 3 | 3 | 3 | 2 | 20 |
| V | INTRATHORACIC BLOOD PUMP WITH THORACIC/ ABDOMINAL NUCLEAR POWER | 2 | 3 | 2 | 1 | 3 | 3 | 0 | 14 |
| BOTH INTERNAL & EXTERNAL COMPONENTS WITH SKIN INTACT | | | | | | | | | |
| VI | INTRAVENTRICULAR ELECTRIC (TRANSCUTANEOUS) | 4 | 3 | 4 | 3 | 3 | 3 | 3 | 23 |
| VII | INTRATHORACIC ELECTRIC (TRANSCUTANEOUS) | 4 | 3 | 3 | 2 | 3 | 3 | 1 | 19 |
| BOTH INTERNAL & EXTERNAL COMPONENTS WITH SKIN PENETRATION | | | | | | | | | |
| VIII | INTRAVENTRICULAR ELECTRIC (PERCUTANEOUS) | 4 | 3 | 4 | 3 | 1 | 3 | 3 | 21 |
| IX | INTRATHORACIC ELECTRIC (PERCUTANEOUS) | 4 | 3 | 3 | 1 | 1 | 3 | 1 | 16 |
| X | INTRAVENTRICULAR PNEUMATIC OR HYDRAULIC | 4 | 3 | 4 | 3 | 0 | 1 | 3 | 15 |
| XI | INTRATHORACIC | 4 | 3 | 3 | 2 | 0 | 1 | 1 | 14 |

TABLE 1-continued

| | PERMANENT CIRCULATORY SUPPORT SYSTEMS | | | | | | |
|---|---|---|---|---|---|---|---|
| AVAIL-ABILITY | HEMO-DYNAMIC FUNCTION | THROM-BUS RISK | SYSTEM RELI-ABILITY | INFECTION/ REJECTION | QUAL-ITY OF LIFE* | COST | TOTAL |
| PNEUMATIC OR HYDRAULIC | | | | | | | |

KEY
4 - EXCELLENT, 3 - GOOD, 2 - FAIR, 1 - POOR, 0 - UNACCEPTABLE
*Quality of Life - Portability, Activities Limits, Maintenance, External Batteries, etc.

Having described the general background and characteristics of intraventricular artificial hearts and methods for their surgical implantation, specific objects of the invention are given in the following section.

OBJECTS OF THE INVENTION

An object of the present invention is to provide an artificial heart capable of sustaining a high quality of life for many years, with a low risk of complications, including thrombus formation, thromboembolism, stroke, infection, blood damage, or mechanical failure of the system.

It is a further object of the invention to provide an artificial heart that can be surgically implanted within the cavity of the natural left ventricle.

It is another object of the invention to provide a method of surgically implanting this type of artificial heart within the left ventricular cavity.

It is an additional object of the invention to provide an intraventricular artificial heart which can be electrically powered.

It is an additional object of the invention to provide an electrically-powered intraventricular heart that requires no compliance device (separate displaced volume chamber).

It is a still further object of the invention to provide intraventricular artificial hearts that function effectively at high heart rates and, therefore, occupy a reasonably small volume.

It is an additional object of the invention to provide artificial hearts that can be implanted within the left and right cavities of the natural heart to replace the function of both ventricles.

It is a further object of the invention to provide intraventricular artificial hearts capable of actuation by a fluid power source outside the particular cavity.

An additional objective is to provide rotary hydrodynamic embodiments of the invention having a bearing system to support the rotor within the blood stream that remains free of thrombus.

It is a still further object of the invention to provide connector systems to facilitate the surgical implantation of intraventricular artificial hearts that permit a seamless blood pump to be used with pusher-plate and fluid-actuated devices.

It is an additional object of the invention to provide surgical connectors for use with rotary-type intraventricular artificial hearts and other artificial hearts that provide a perfectly-aligned, tightly-clamped junction between the polymeric components sewn to the natural tissues and rigid components of the blood pumping device.

It is a further object of the invention to provide a method of fabricating seamless intraventricular fluid-actuated blood pumps having a diaphragm of special design for extended durability. In addition, it is an object to provide a method of fabricating improved diaphragms for other types of artificial hearts.

It is another object of the invention to provide a bearing system including permanent-magnet magnetic axial thrust bearings in combination with a mechanical rotary bearing system to achieve suspension of the rotating element within the bloodstream without excessive thrombus formation or blood damage.

It is a still further object of the invention to provide a radial bearing system capable of rotationally supporting a member within the bloodstream without excessive blood damage or thrombus formation that utilizes a wire maintained in tension as the shaft of a journal bearing system.

An additional object of the invention is to provide an artificial heart that is inherently durable and reliable and is capable of pumping continuously for periods in excess of ten years.

Another object of the invention is to provide intraventricular artificial hearts that are powered directly by contraction of electrically-stimulated transplanted or grafted muscle or that may be powered by such muscle indirectly through the use of hydraulic fluid coupling.

It is a still-additional object of the invention to provide muscle-powered artificial hearts that may be initially powered by a supplementary external heart-drive system during the period of time the muscle is being conditioned and thereafter, without major surgery, may be converted to be powered solely by the muscle.

It is a further object of the invention to provide intraventricular artificial hearts that can be manufactured at a relatively low cost.

It is a still-further object of the invention to provide an artificial heart that requires only one prosthetic heart valve to be used and permits the patient's aortic valve to be saved unless the valve is diseased.

It is an additional object of the invention to provide an artificial heart with a minimum surface area of contact of prosthetic materials, both with the blood and with other tissues.

It is a still-further object of the invention to provide an artificial heart with a porous exterior surface into which vascularized connective tissue will grow.

It is an additional object of the invention to provide an artificial heart with redundancy to allow adequate function in the event of failure of one or more of its components in order to save the patient's life until the system can be replaced.

It is also an object of the invention to provide surgical methods of implantation of intraventricular artificial hearts that permit the surgery to be done with minimal bleeding.

These, and additional objects of the present invention, will be more fully understood by referring to the drawings and specific descriptions in the following sections.

THE DRAWINGS

FIG. 1 is a schematic illustration of the heart viewed in the anterior-to-posterior direction indicating the chambers of the right and left ventricles.

FIG. 2 is a cross-section of the natural heart taken along section AA of FIG. 1.

FIG. 3 is a cross-section of a natural heart with an intraventricular artificial heart implanted within the left ventricular chamber. FIG. 3 is taken along section AA of FIG. 4.

FIG. 4 is a schematic lateral view of the natural heart showing an intraventricular artificial heart implanted into the left ventricular cavity and also showing a prosthetic tissue mitral valve implanted into the mitral valve annulis of the natural heart.

Figure 12:
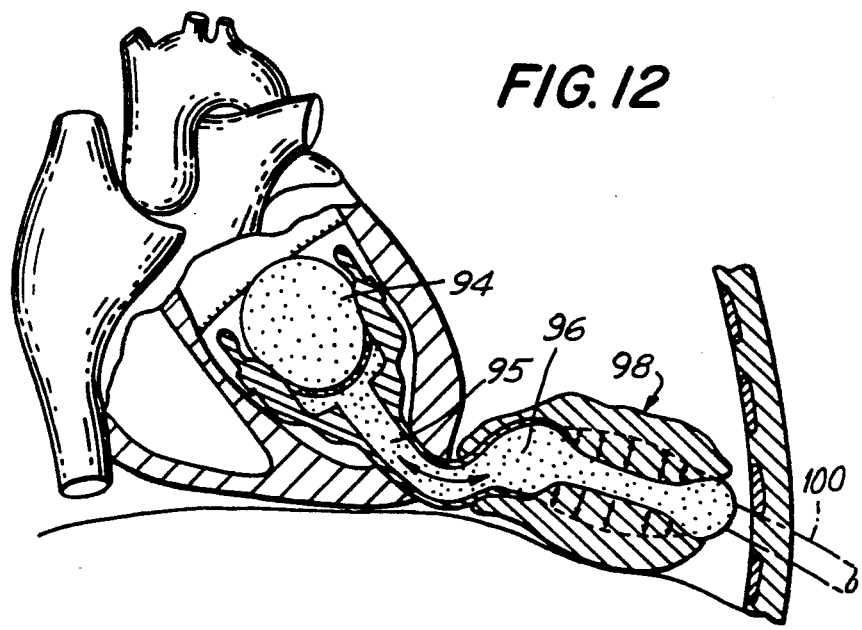

FIG. 12 is a schematic partially-sectional view of the natural heart and left side of the thoracic cavity showing a hydraulically-actuated intraventricular blood pump implanted within the cavity of the left ventricle and a compressible hydraulic fluid-filled balloon implanted in the left thorax surrounded by contractile muscle tissue arranged to compress the balloon and thereby pump the artificial heart when it is electrically stimulated.

Figure 13:
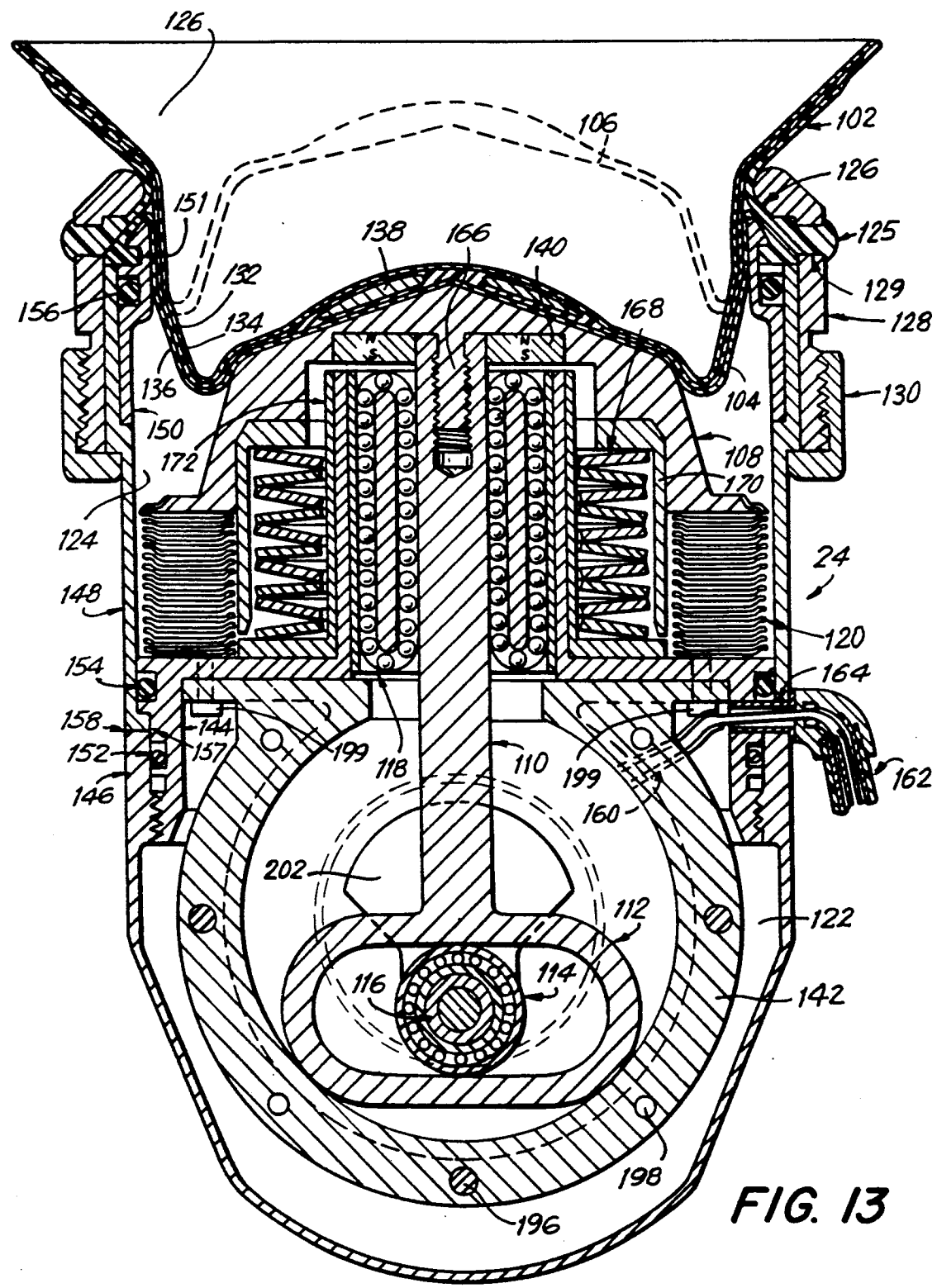

FIG. 13 is a longitudinal sectional view of a pusher-plate-type rolling diaphragm intraventricular artificial heart. The mechanism is shown in the end-diastolic position with the end-systolic position of the diaphragm indicated in dotted lines.

Figure 14:
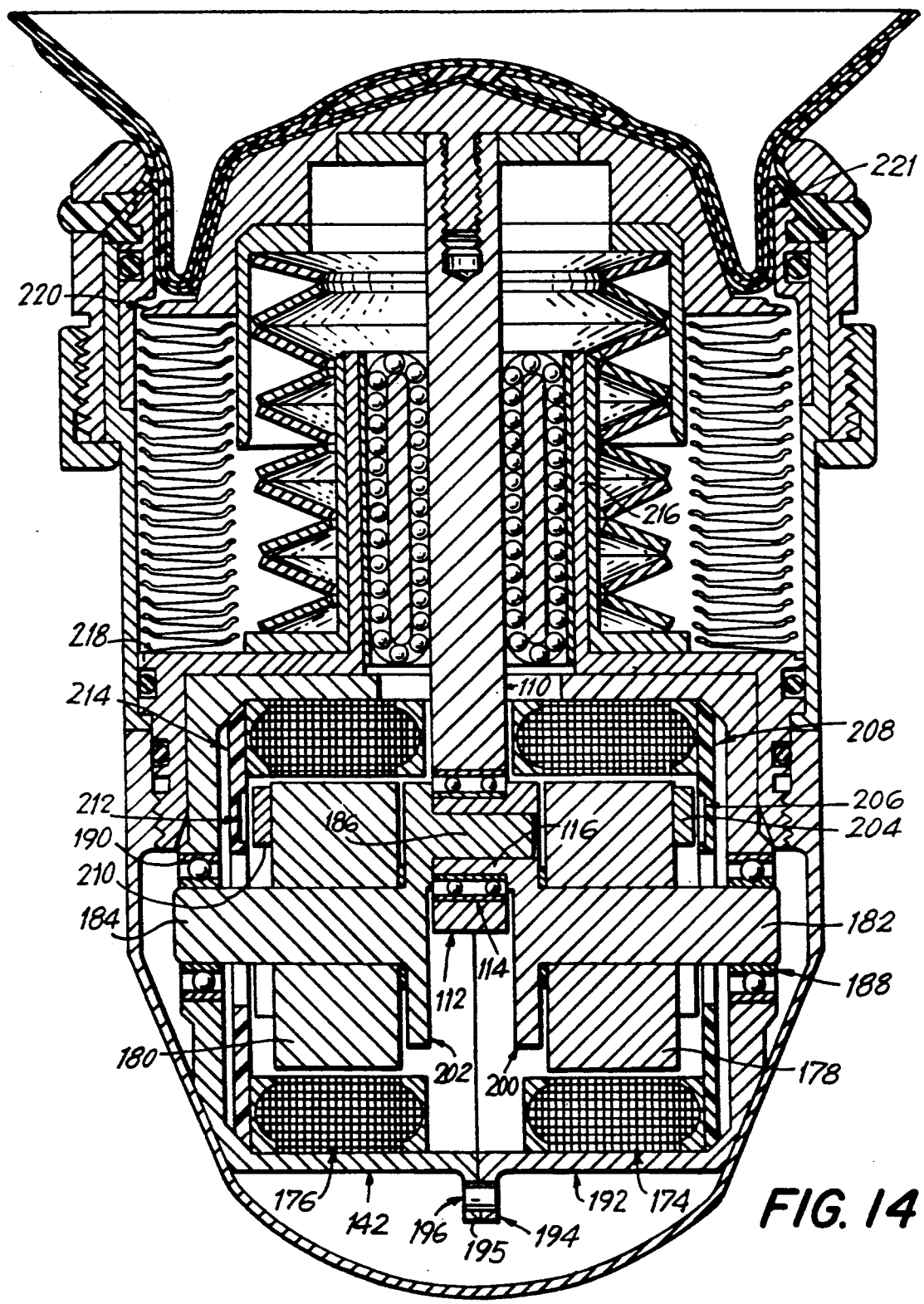

FIG. 14 is a longitudinal sectional view of the device illustrated in FIG. 13 at ninety degrees of rotation to the position shown in FIG. 13. The pusher-plate and mechanism is shown in the end-systolic position.

FIG. 15 includes a series of schematic diagrams of pusher-plate or hydraulically-activated artificial hearts. The diagrams represent elements of generally cylindrical form in longitudinal section and show chambers filled with gas, hydraulic fluid, and blood. FIGS. 15-A and 15-B represent an illustrative pair, as do FIGS. 15-C and 15-D, and FIGS. 15-E and 15-F, and FIGS. 15-G and 15-H. FIG. 15-I is a schematic illustration of a hydraulic actuator and an intraventricular artificial heart.

FIG. 16 is a graph of the relationship between the distance moved by the pusher-plate in FIG. 15-G and 15-H and the volume displaced by the pusher-plate.

FIGS. 17A–17E represent graphically the relationships between the principal fluid, gas, and mechanical forces acting on the pusher-plate of an intraventricular artificial heart as a function of the angular position of rotation of the motor and crankshaft driving the pusher-plate throughout one cardiac cycle (one heartbeat, both filling and ejection).

FIG. 18 is a partially-exploded three-dimensional representation of the rotor and pump impeller of a centrifugal-type intraventricular artificial heart utilizing a wire in tension as the shaft of a rotary bearing system.

FIG. 19 is a three-dimensional view of the rotor and impeller of an axial flow pump-type intraventricular artificial heart utilizing a wire in tension as the shaft of the rotary bearing. The pump outflow stators are also shown.

FIG. 20 is a schematic three-dimensional view illustrating the crank and scotch yoke mechanism of a pusher-plate-type intraventricular artificial heart, the two electric motors that power the heart, and the main shaft supported on a linear ball-bearing (ball-bushing).

FIG. 21 illustrates characteristics of belleville washers utilized in the embodiment of an intraventricular artificial heart shown in FIGS. 13 and 14. FIG. 21-A is an end view of a stack of belleville washers; FIG. 21-B is a generalized plot of the load versus deflection for belleville washers; FIG. 21-C represents a stack of belleville washers in series; FIG. 21-D represents a combination of washers stacked both in parallel and in series.

FIG. 22 is a cutaway longitudinal sectional view of the blood diaphragm and connector assembly of the intraventricular artificial heart shown in FIGS. 13 and 14, indicating the magnetic coupling of the blood diaphragm assembly to the pusher-plate.

FIG. 23 is an enlarged longitudinal sectional detail view of the air vent tube at the junction of the connector and blood diaphragm assembly to the artificial heart housing.

Figure 27:
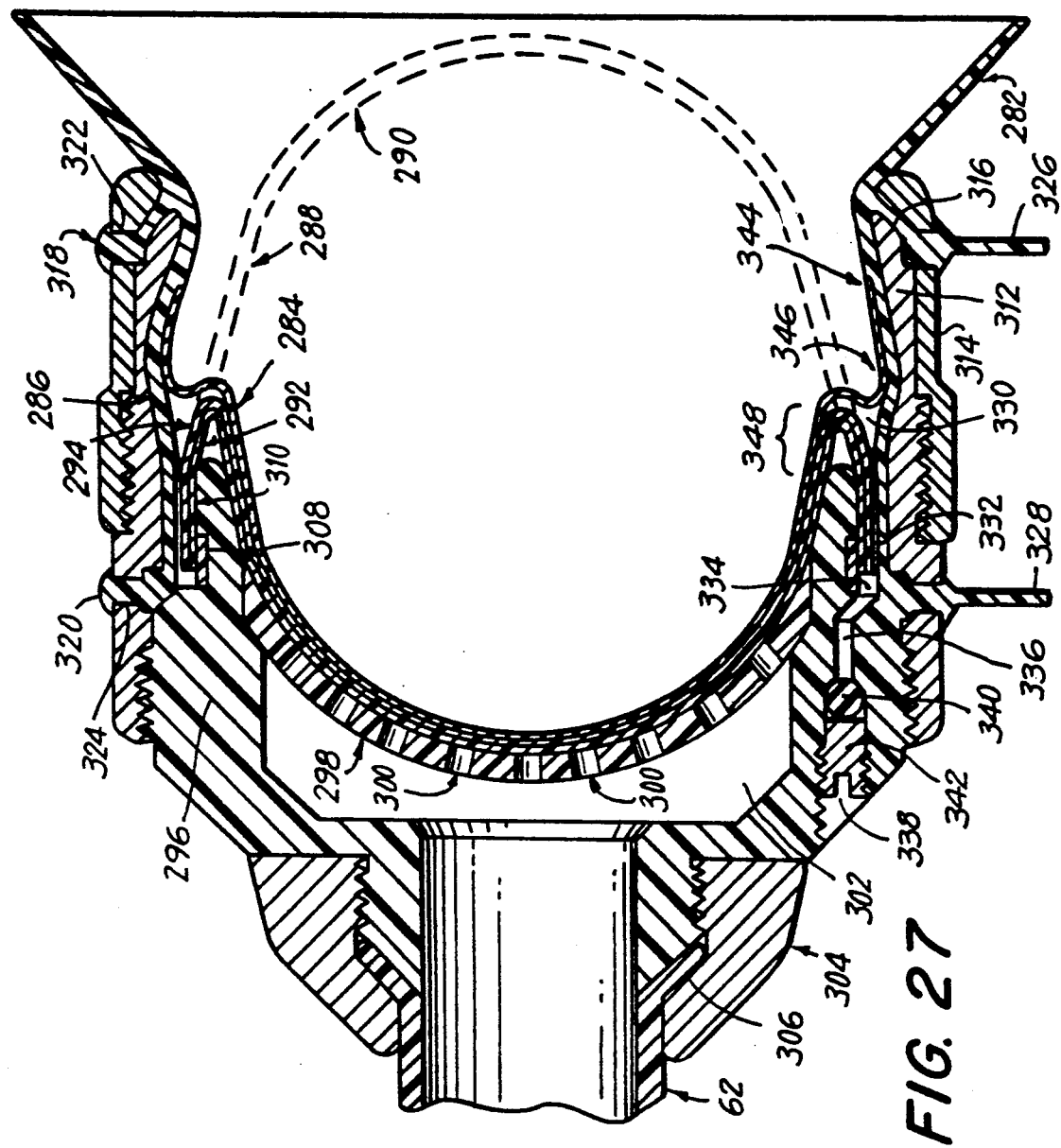

FIG. 24 is a cutaway longitudinal sectional view of the blood diaphragm and the polymer part of the housing and sewing ring of the intraventricular artificial heart in FIG. 27. FIG. 24 also shows the mold assembly utilized to solution-cast the blood diaphragm in contact with a portion of the polymer housing and sewing cuff.

FIG. 25 is a cutaway longitudinal sectional view of an artificial heart housing, a blood diaphragm, and a blood diaphragm mold of the type utilized with the prior art JARVIK 7 ® artificial heart.

FIG. 26 is a partially cutaway longitudinal sectional view of an artificial heart housing, blood diaphragm, and mold illustrating an improved design and its method of fabrication.

FIG. 27 is a longitudinal sectional view of an intraventricular artificial heart actuated by fluid power from a remote source.

Figure 28:
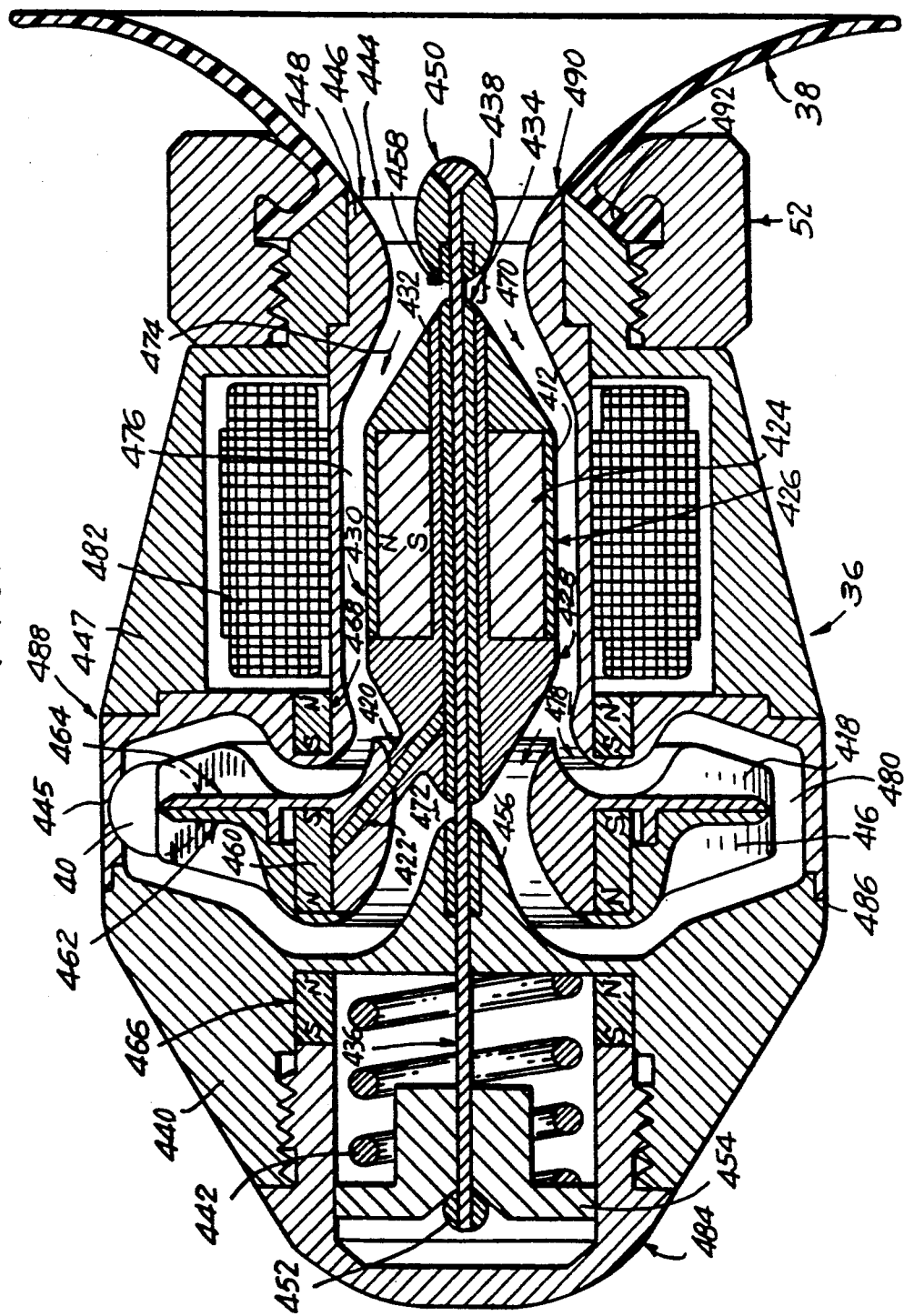

FIG. 28 is a longitudinal sectional view of a rotary intraventricular artificial heart having a centrifugal-type impeller and a radial bearing system which uses a wire in tension together with an axial bearing system comprised of magnets with opposing poles.

Figure 29:
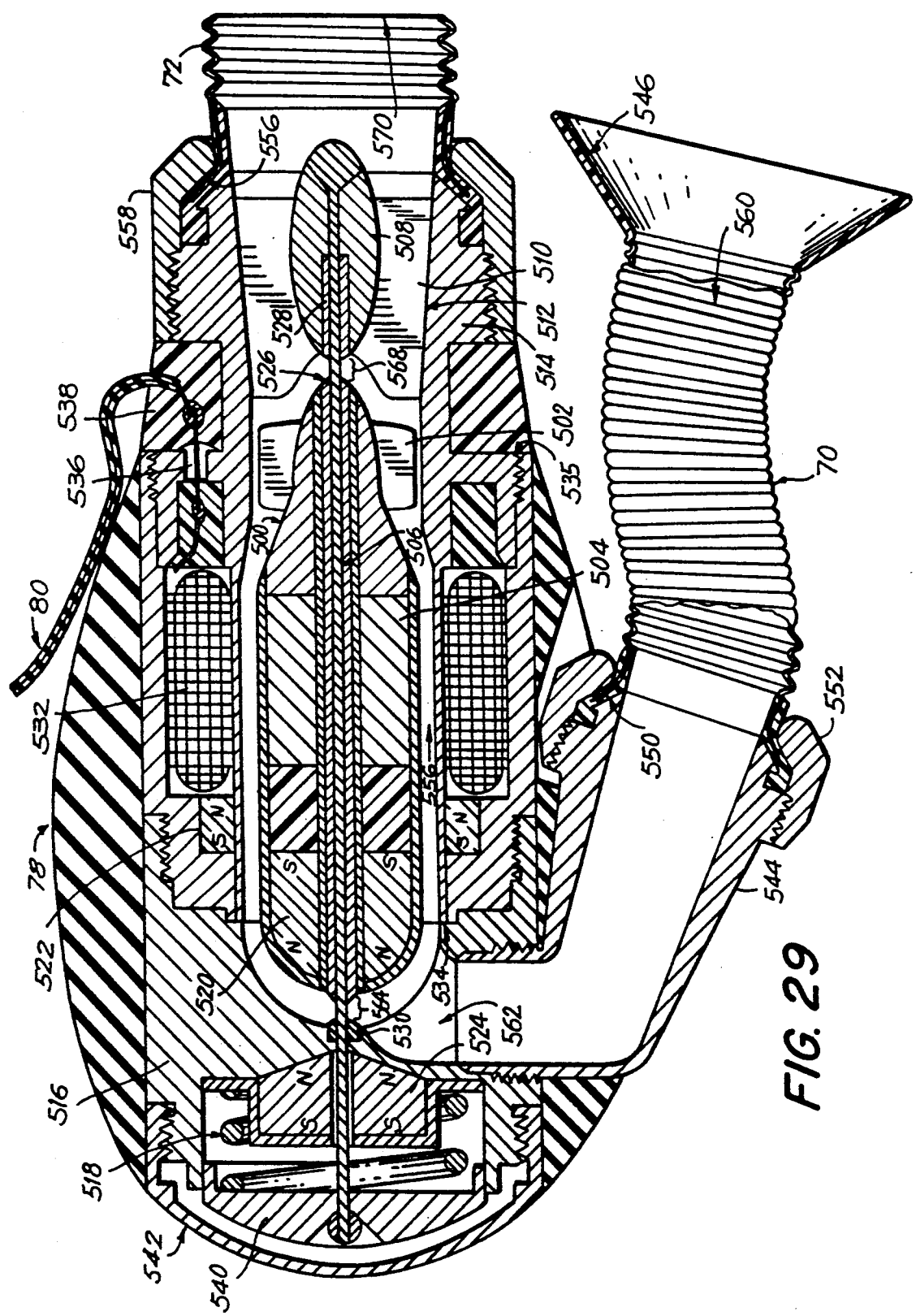

FIG. 29 is a longitudinal sectional view of an intraventricular artificial heart of the rotary type utilizing an axial flow pump and a bearing system similar to that illustrated in FIG. 28.

FIG. 30 is a longitudinal section of an intraventricular compressible blood sac utilized in combination with a skeletal muscle graft to constitute an intraventricular artificial heart. FIG. 30-B is the top view of the blood chamber shown in FIG. 30-A. FIGS. 30-C and 30-D are sectional views of the blood chamber shown in FIG. 30-A, taken along line AA. FIG. 30-C shows the blood chamber in end-diastolic position completely full of blood, and FIG. 30-D shows the shape of the chamber during systolic contraction while its volume is being reduced.

FIG. 31 is a partially cut-away schematic view of a muscle-powered intraventricular artificial heart utilizing the blood chamber illustrated in FIG. 30-A.

FIG. 32 is a partially cut-away schematic view of a muscle-powered intraventricular artificial heart in which part of the natural left ventricle has been cut away and replaced with muscle graft.

FIG. 33A is a longitudinal section of a muscle-powered intraventricular artificial heart of the axio-symmetric type utilizing hydraulic fluid coupling between the outer compressible wall and the inner blood chamber. FIG. 33-B is a sectional view of the device in FIG. 33-A taken along line AA. FIG. 33-B shows the device in the full-fill (end-diastolic) position. FIG. 33-C is a cross-sectional view also taken along section AA of FIG. 33-A, showing the device in the full-eject (end-systolic) position.

FIG. 34 is a lateral view of a muscle-powered intraventricular artificial heart of the hydraulically-coupled axio-symmetric type. The figure shows the replacement of the mitral valve with a prosthetic tissue valve and the utilization of a large skeletal muscle graft to replace a portion of the wall of the natural left ventricle.

FIG. 35 is an assembly drawing showing the inner blood chamber of the axio-symmetric muscle-powered blood pump and the connector assembly used for its attachment to the outer housing.

GENERAL DESCRIPTION OF THE INVENTION

Intraventricular artificial hearts are blood pumps that are placed within the chamber of the left or right ventricle, or both. The normal anatomic relationships of flow into and out of the heart are retained, and the natural support of the heart by the mediastinal and pericardial structures is utilized to support the artificial device. In general, a pumping mechanism is connected in place within the ventricular chamber utilizing a sutured connector or pair of connectors. With pulsatile-type pumps, valves may be included in the artificial heart, but it is preferable to utilize tissue valves sewn into the natural heart in the inflow position and to retain the patient's natural valves in the outflow position. Thus, the connection to a pulsatile intraventricular artificial heart may involve only one suture line, and the entire blood surface of the device can be completely seamless. Since the valves used are implanted into the natural heart in the same positions where prosthetic heart valve replacements have been used in many tens of thousands of patients over the last three decades, extensive data shows that their use in this position is associated with a very low risk of complications. Thus, by positioning the valves in the natural locations and by implanting the pulsatile blood pump within the ventricular cavity, the hemodynamic flow path is very close to normal.

Rotary hydrodynamic intraventricular artificial hearts (utilizing axial-flow, mixed-flow or centrifugal-flow pumps) do not require valves. In this application, the leaflets of the inflow valves are surgically excised. The outflow valve leaflets ar also surgically excised if an outflow graft is surgically attached to the inside of the ventricle, or the outflow valve leaflets may be sutured together if an outflow graft is used to connect the outflow of the intraventricular pump to the aorta or pulmonary artery above the level of the natural valve.

Intraventricular blood pumps must be very compact in design and must have an anatomic shape compatible with implantation in the ventricular chamber. In many cases, the left ventricle will be markedly enlarged in patients who have experienced a prolonged period of heart failure. This can provide additional space, but in general, pulsatile artificial heart pumps must operate at a high heart rate with a relatively low stroke volume in order to be made small enough to fit within the heart. Rotary blood pumps must be designed to reasonably conform to the natural anatomy. In the case of muscle-powered intraventricular blood pumps, part of the left ventricular wall may be removed and replaced with a skeletal muscle graft. The surgical techniques used for implantation of intraventricular artificial hearts must preserve the blood supply to the remaining natural heart to maintain the intraventricular septum and right heart muscle tissue in good condition and to provide blood to the left ventricular muscle to retain its health and to prevent infection.

FIG. 1 represents the natural heart as viewed in the anterior-posterior direction and indicates the general form of the chambers. The left ventricular chamber 2 is generally ovoid in form and has a length of approximately six to twelve centimeters, depending on the size of the individual patient and the state of health of the heart. The right ventricular chamber 4 and right ventricular muscle wall 8 wraps around the left ventricular chamber as best seen in FIG. 2 and is separated from the left by the intraventricular septum 10. The wall of the left ventricle 6 is generally thicker than the wall of the right ventricle 8 but may become replaced with a significant amount of scar tissue following major heart attacks and become thinned.

Each ventricular chamber is entered through the oval annulis of the inflow valve which are named the tricuspid valve on the right side 12 and the mitral valve on the left side 14. These valves have long, filament-like attachments to the leaflets called chordae tendineae, which connect to projections of the myocardium within the ventricular cavities called papillary muscles. Intraventricular artificial hearts would generally interfere with the chordae tendineae and papillary muscles and thus interfere with valve function. Therefore, in designs requiring inflow valves, the chordae tendineae and the natural inflow valve leaflets must be excised and replaced with artificial valves. The outflow valves of the natural heart are the aortic valve 18, which prevents back flow of blood from the aorta 16 into the left ventricle during diastole and the pulmonic valve 22, which prevents back flow of blood from the pulmonary artery 20 into the right ventricle during diastole.

In FIG. 3, the cross-sectional shape of the intraventricular artificial heart 24 generally conforms to the natural round cross-sectional shape of the left intraventricular chamber. The septum 10 is thus supported in its natural position, and ventricular function is retained near normal. If the shape of the intraventricular artificial heart does not support the intraventricular septum sufficiently, right ventricular function will deteriorate.

FIG. 4 shows a pulsatile rolling diaphragm-type of intraventricular blood pump as seen in the lateral view of the heart (representing the view seen in the lateral chest X-ray). The blood pump is connected in place by sutures between the diaphragm sewing ring assembly 26 and the housing of the pump. The screw on connector 28 is used to fasten the sewing ring to the housing. The device is powered by electric energy supplied through the electric cable 30, which is surgically brought through the wall of the ventricle and may exit the chest through a percutaneous lead or may be connected to the internal coil of a transcutaneous energy-transmission device. A prosthetic valve 32, in this illustration a tissue valve, is sutured into the annulis of the mitral valve. A small air vent tube 34, utilized to evacuate the air between layers of the pump diaphragm system, is plugged off and lies within the ventricular chamber.

Figure 5:
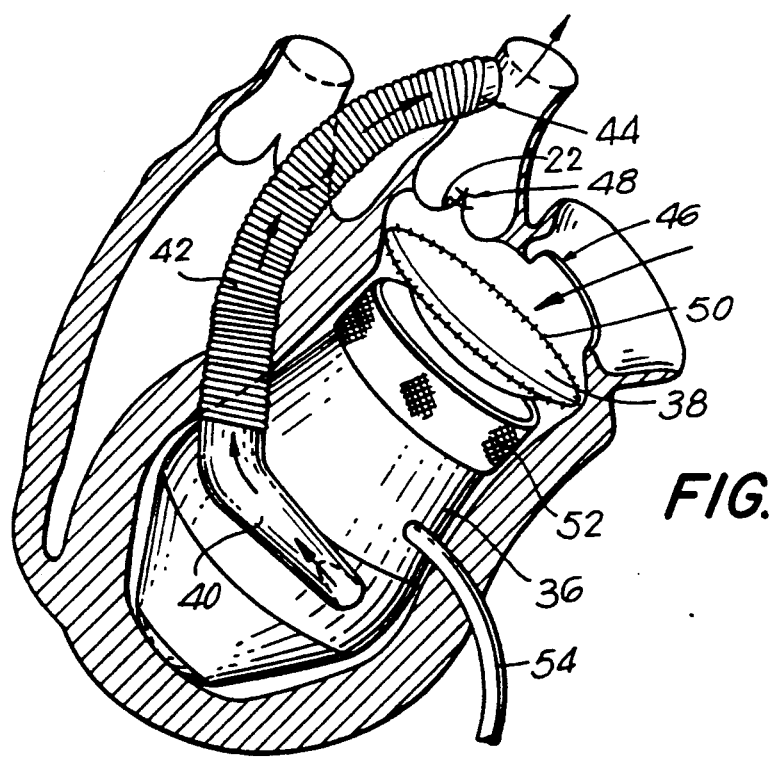
FIG. 5 is a schematic lateral view of a natural heart with an intraventricular artificial heart of the centrifugal type implanted in the left ventricular chamber with the outflow graft connected to the aorta.

FIG. 5 illustrates the implantation of a centrifugal-type intraventricular artificial heart. The blood pump, generally indicated at 36, conforms well to the shape of the intraventricular cavity. The inflow of blood enters through the sewing ring 38, is acted upon within the pump by a centrifugal impeller powered by an electric motor, and the blood exits the pump through the outflow diffuser 40, flows through the outflow graft 42, and enters the aorta through an end-to-side anastomosis 44 just above the aortic valve. Since the device is the rotary type, it requires no inflow or outflow valves. Therefore, the leaflets of the mitral valve are excised 46, and the leaflets of the aortic valve are fastened together in the closed position with sutures 48. The inflow sewing cuff 38, sutured around both the annulis of the mitral valve and the outflow track of the aorta as shown at 50, is attached to the pump housing by a screwon connector ring 52. Power is brought to the electric motor within the pump through the power cable 54.

Figure 6:
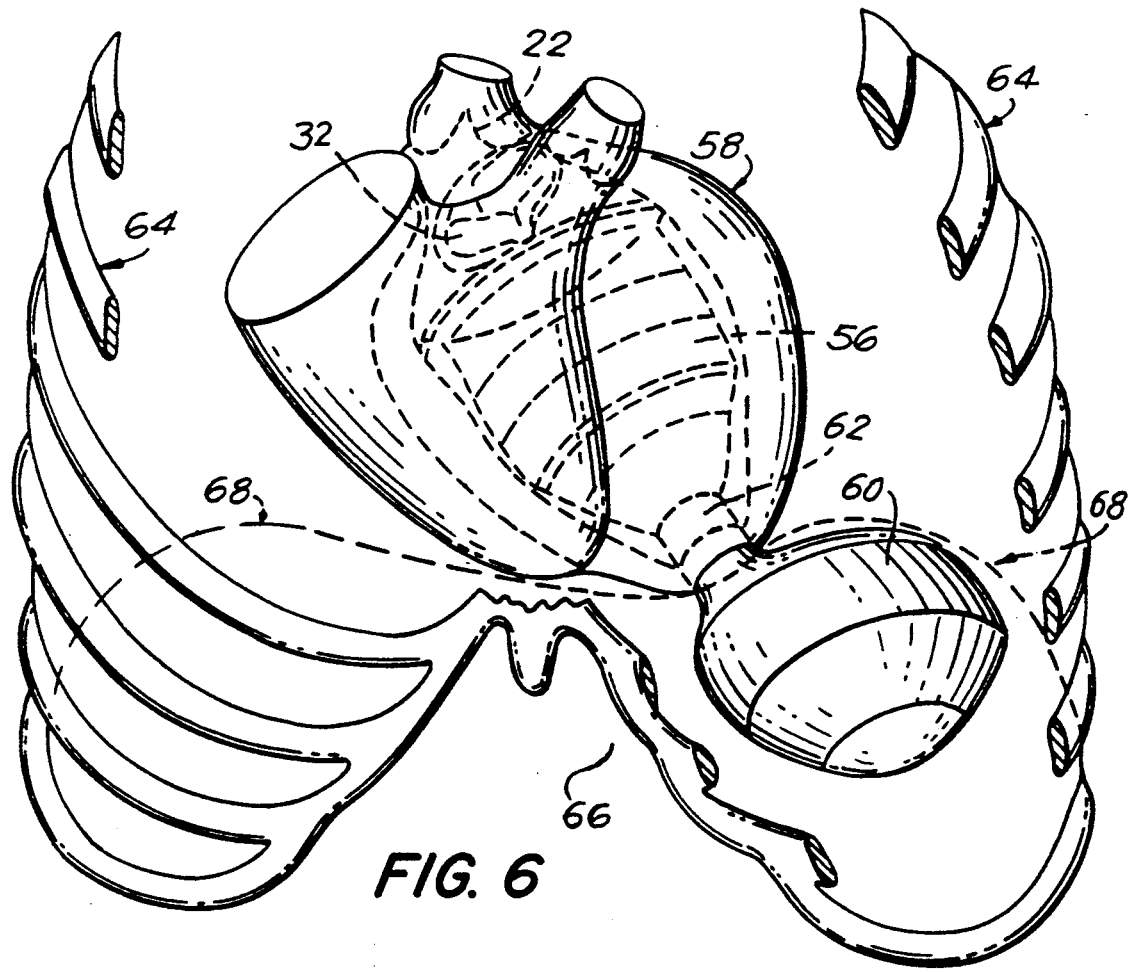
FIG. 6 is a partially cut-away anterior-posterior view of the thorax, showing an intraventricular artificial heart implanted within the left ventricle, powered by an electrohydraulic energy-converter implanted in the abdominal cavity immediately below the diaphragm.

FIG. 6 illustrates an intraventricular artificial heart pump 56 actuated by a remote electro-hydraulic energy-converter 60 located in the abdominal cavity 66 below the diaphragm 68. A short hydraulic fluid conduit 62 crosses the diaphragm and the apex of the natural heart. In this figure, the natural left ventricle 58 is shown approximately normal size in relation to the rib cage 64. With heart failure, the lateral border of the left ventricle may be displaced as the heart enlarges, sometimes practically filling the rib cage on the left side.

Figure 7:
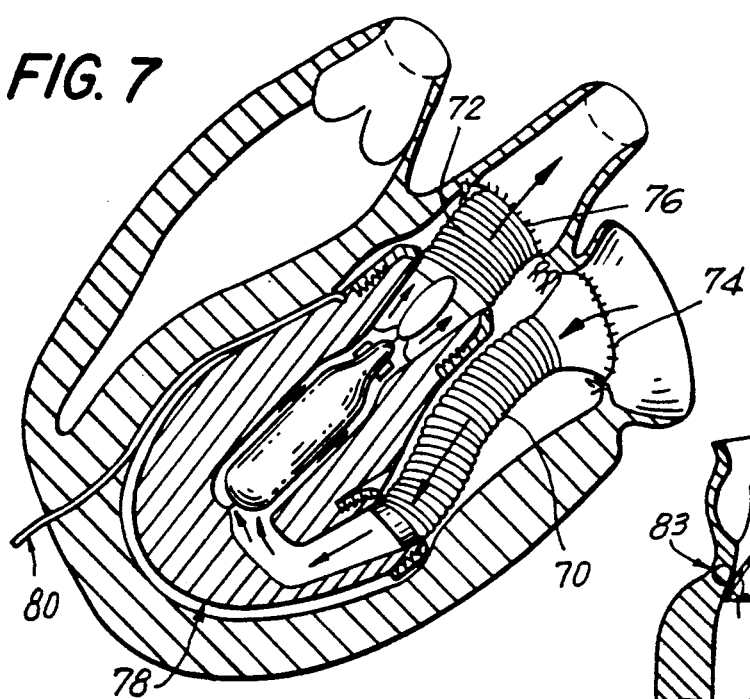
FIG. 7 is a lateral schematic sectional view of a natural heart with an intraventricular artificial heart of the axial flow pump-type implanted within the left ventricular chamber.

FIG. 7 illustrates an axial flow pump-type intraventricular artificial heart within the chamber of the left ventricle. In this embodiment of the invention, the blood pump 78 has a configuration similar to that of the chamber of the left ventricle. The leaflets of both the aortic valve and the mitral valve are excised. Individual connectors are sutured for the inflow and outflow grafts. The inflow connector is sutured to the annulis of the mitral valve 74 and brings the blood into the artificial heart through the graft 70. The outflow connection is made near the root of the aorta at suture line 76, within the ventricle, which brings the blood out of the artificial heart to the aorta through the outflow graft 72. Since both the inflow and outflow grafts and suturing cuffs are made of a soft flexible material, such as polyurethane and dacron, they are turned inside-out in the actual suturing procedure. Thus the inflow cuff is placed mostly within the left atrium during the suturing procedure, and after the suture line is finished, it is pulled through itself like turning a sleeve inside out. A similar technique is used with the aortic graft.

Figure 8:
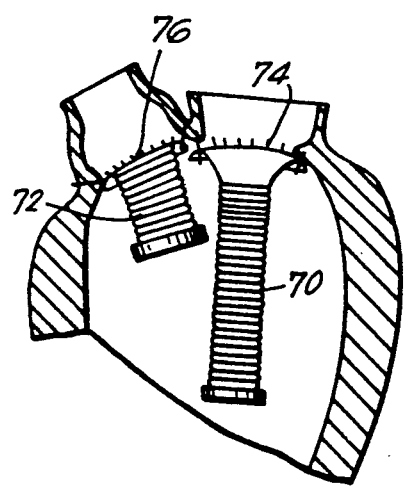
FIG. 8 is a cutaway sectional view of the natural left ventricle with connectors for attachment of an intraventricular artificial heart sutured to the openings of the mitral valve annulis and the root of the aorta.

FIG. 8 illustrates the position of the grafts and connectors in the left ventricle after the suturing is completed.

Figure 9A:
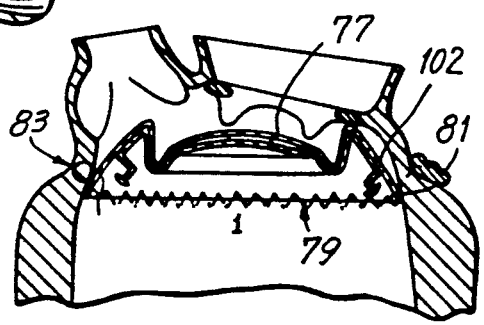
FIG. 9A is a cutaway sectional view of the natural left ventricle with the sewing ring and blood diaphragm assembly of a pusher-plate intraventricular artificial heart surgically sutured in position.
Figure 9B:
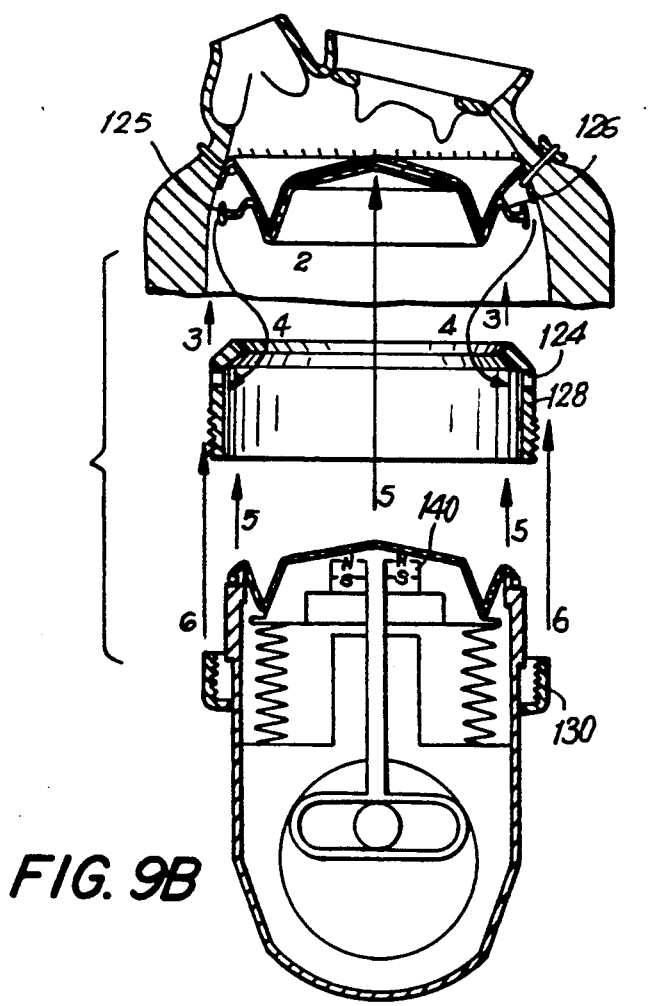
FIG. 9B is a schematic partially cut-away sectional view of the left ventricle, a pusher-plate intraventricular artificial heart, and the connector elements, indicating the order of surgical implantation and sequence of assembly.

FIG. 9-A illustrates the method of surgical implantation of the pulsatile intraventricular blood pump illustrated in FIGS. 13 and 14. After the chest is opened and a large incision is made in the wall of the left ventricle, the leaflets of the mitral valve and the chordae tendineae are excised. A prosthetic mitral valve is then sutured into place through the incision in the ventricular wall. After the prosthetic valve implantation is completed, the suture ring and blood diaphragm is partially inverted as shown in FIG. 9-A and placed within the ventricle close to the mitral and aortic valves. The diaphragm can only be partially inverted because of its rigid central portion 77. The sewing cuff 102 is then sutured to the wall of the ventricle with interrupted and running sutures 79. Felt pledgets 81 are used to reinforce the suture line from the outside of the heart where exposure permits.

The suture line is maintained close to the aortic valve on the septal side at 83, to avoid passing the sutures through the electrical conductive fibers of the bundle of His. In the event that these conductive fibers are damaged, right heart function may be impaired, and a pacemaker for the right heart may be required. After the suture line is completed, a small cannula is inserted through the aortic wall and across the aortic valve to make the valve incompetent. The cross-clamp on the aorta is then released to pressurize the intraventricular cavity between the mitral valve and the implanted diaphragm and connector. This procedure permits leaks in the suture line to be detected and repaired before connection of the intraventricular blood pump.

After the suture line is completed and tested and the aorta is again cross-clamped, it is time to connect the artificial heart to the diaphragm sewing cuff assembly. FIG. 9-B illustrates this procedure. The sewing ring cuff includes a connecting flange 126 as seen in FIGS. 13 and 22. Several small snap-fit fasteners 125 are attached, spaced around the connecting flange 126. A rigid connector clamping ring 128 is then inserted into the ventricle and positioned around the connecting flange. The connecting flange, made of a flexible polymer or fabric, can be folded and crumpled to fit through the smaller opening of the connector clamping ring. The snap-fit fasteners 125 are then aligned with the holes 29 in the clamping ring and pushed through. This is illustrated by the arrows labelled 4 in FIG. 9-B. These connectors hold the sewing cuff in the proper position and alignment with regard to the connector clamping ring 128. The pump mechanism and housing is then positioned against the blood diaphragm indicated by the arrows 5 in FIG. 9-B and fastened to the connector clamping ring with the screw fastener nut 130.

When the pusher-plate is placed close to the blood diaphragm assembly, magnets 140 in the pusher-plate attract the magnetic metal washer 138, which is embedded in the blood diaphragm. Air may be trapped between the blood diaphragm 280 and the hydraulic fluid diaphragm 136 as illustrated in FIG. 23. The trapped air may form a bubble between these diaphragm layers as indicated at 276 in FIG. 23. A small air vent tube 34 attached to the connector skirt has a hole 274 at the junction of the housing to the connecting flange 126 that permits air to escape. This tube passes through a notch 284 in the connector clamping ring 128. After the screw clamping ring 130 is tightened, a syringe is used to draw air through the tube as indicated by the arrows 278 in FIG. 23. Still referring to FIG. 23, as the air bubble 276 is reduced, the blood diaphragm moves from an improperly-seated position 280 to a properly-seated position 282 in smooth, uniform contact with the hydraulic fluid diaphragm. The space between these two contacting membranes may be lubricated with dry powdered graphite, applied at surgery during final attachment.

Figure 10:
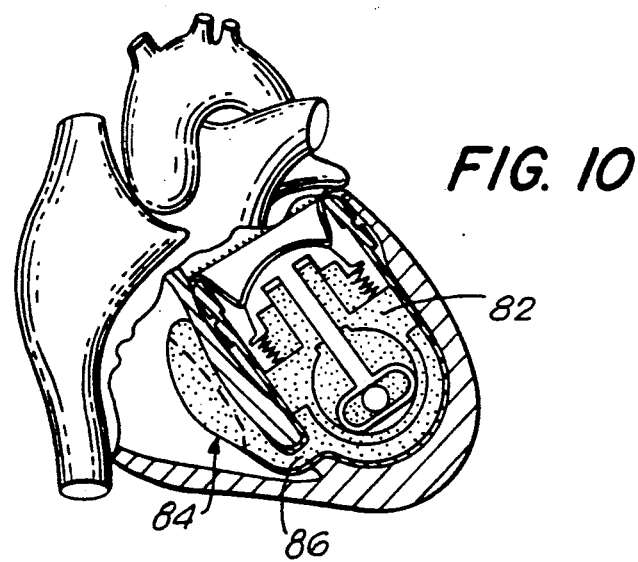
FIG. 10 is a schematic sectional view of a natural heart with a pusher-plate-type intraventricular artificial heart implanted within the left ventricle and a hydraulic fluid-filled compliance balloon implanted within the cavity of the right ventricle.

The method of implantation and connection of intraventricular artificial hearts may vary depending upon the specific design used. Different embodiments may incorporate right ventricular as well as left ventricular blood pumps. FIG. 10 illustrates an intraventricular total artificial heart utilizing implantation of a pusher-plate blood pump 82 in the left ventricular chamber with hydraulic fluid actuation of a right ventricular pumping sac 84 via a hydraulic fluid conduit tube 86. In operation, this biventricular total artificial heart alternately pumps the right and left ventricles.

Figure 11:
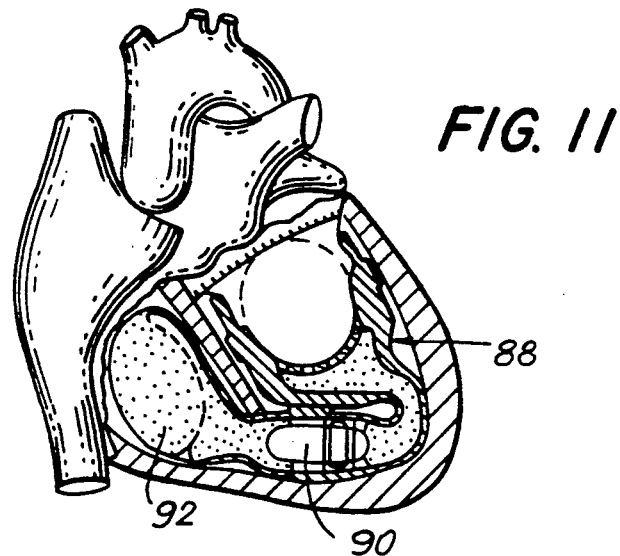
FIG. 11 is a schematic partially-sectioned view of an electro-hydraulic intraventricular artificial heart with the left ventricular blood pump and electro-hydraulic energy-converter implanted within the chamber of the left ventricle and the right ventricular pumping diaphragm implanted within the cavity of the right ventricle.

With devices incorporating a major pumping chamber within the right ventricle, such as those illustrated in FIG. 10 and FIG. 11, it is necessary to remove the tricuspid valve leaflets and chordae tendineae and replace the tricuspid valve with a prosthetic implant. The hydraulically-actuated pumping diaphragms or sac devices implanted within the right ventricle may take the form of a free balloon where the stroke volume is relatively small, such as 25 ml, in the embodiment shown in FIG. 10, or may utilize a diaphragm-type pump, sutured to the myocardial wall or the intraventricular septum to permit a larger stroke volume with lower risk of thrombus formation. The device illustrated in FIG. 11 shows as intraventricular blood pump 88 having a stroke volume of approximately 50 ml that is powered by a reversing electro-hydraulic energy-convertor 90 capable of alternately pumping fluid between the left intraventricular blood pump 88 and a diaphragm-type right heart intraventricular blood pump 92 implanted within the cavity of the right ventricle. Although not illustrated, in an embodiment of this type, the right ventricular blood pump may incorporate a sewing cuff and diaphragm similar to that utilized with the left ventricular blood pump 88. This sewing cuff and diaphragm together with its connector design is illustrated in FIG. 27.

A similar device having the type of connector assembly shown in FIG. 13 could be used with this embodiment. The surgical procedure would include the excision of the mitral valve, implantation of a prosthetic mitral valve, the surgical suturing of the sewing cuff with the left heart diaphragm and connector flange, and testing the suture line for leaks. Next, the right ventricular surgery would be performed, including the excision and replacement of the natural tricuspid valve with a prosthetic valve, and the suturing and leak-testing of the right ventricular sewing cuff diaphragm and connecting flange assembly. Thereafter, the left ventricular pump housing would be fastened to the left sewing cuff and connector assembly, and, finally, the right ventricular device would be affixed to its sewing cuff and connector assembly via a connector clamping ring and screw-fastener nut. With this type of intraventricular total artificial heart implant, alternate pumping of the right and left ventricles at heart rates of approximately 100 to 175 beats per minute would be utilized. The wall of the right ventricular which would remain, and form part of the ventricular cavity, would be compliant and introduce some compliance losses into right heart function. Utilizing a pacemaker, the degree of compliance loss could be varied to achieve balance of right and left cardiac output. If necessary, a leaky mechanical prosthetic pulmonary artery valve could be implanted to introduce further inefficiencies in rightsided pumping and thereby balance the left-to-left shunt which exists due to the bronchial circulation.

FIG. 12 illustrates the use of an intraventricular blood pump, actuated by hydraulic fluid, powered via a muscle graft 98 implanted within the thorax. The muscle graft may be a muscle from the shoulder, back, or body wall. It is dissected free and together with a pedicle containing its nerves, and a blood supply is repositioned within the chest and grafted around a hydraulic fluid sac 96 which communicates through a tube 95 to the hydraulic fluid chamber 94 of the intraventricular blood pump. Upon contraction of the muscle, the hydraulic fluid is forced through the tube and pushes the diaphragm which expels blood from the left ventricle. When the muscle relaxes, the blood pressure filling the left ventricle forces the hydraulic fluid back through the tube into the sac 96. Such a sac may be designed with resilient means to return it to the full position and provide suction to the hydraulic fluid and suction to the blood entering the left ventricle.

If skeletal muscle is repeatedly stimulated with a volley of electric pulses, it will gradually develop characteristics more similar to cardiac muscle when it is properly stimulated over a period of weeks. The muscle develops a larger number of mitochondria involved in the supply of energy to the muscle and develops much greater resistance to fatigue with repeated contraction. However, since it takes approximately six weeks to condition the muscle sufficiently to permit it to take over the workload of the heart, it may be necessary to provide a temporary additional support of power for this system during the period of time the muscle is being conditioned. If the surgery is elective and there is time to precondition the muscle over a period of weeks before the artificial heart is implanted, this temporary support may not be necessary.

The device illustrated in FIG. 10 incorporates a tube 100 that exits the body through the chest wall. During the period of time that the muscle is being conditioned, the intraventricular blood pump may be powered from an external heart driver using either compressed air or hydraulic fluid actuation. Hydraulic fluid is preferred because the tube 100 can periodically be clamped to permit the muscle graft to perform the workload of the heart. Thus its function can be assessed, and it can gradually be employed to take over the full workload of the heart. When the patient is completely weaned from the need of external power support, the tube 100 is sealed and implanted under the skin. A simple pneumatic-to-hydraulic convertor may be utilized outside the chest connected between tube 100 and a conventional pneumatic heart driver such as the type used to power the JARVIK 7 ® heart.

These general descriptions illustrate that there are a wide variety of specific embodiments of the invention that may be employed. To further understand the detailed features and function of several preferred embodiments, these will now be described in detail in the following section.

SPECIFIC DESCRIPTION OF THE PREFERRED EMBODIMENTS

Embodiments of four major types of intraventricular artificial hearts will be described. These major types include pusher-plate, rotary (hydrodynamic axial-flow, mixed-flow or centrifugal-flow pumps), fluid-actuated, and direct muscle-powered devices.

FIGS. 13, 17, 20 and 21 illustrate the design and function of the preferred pusher-plate embodiment. The invention incorporates a rolling diaphragm 104 that moves between an end-diastolic position shown in FIG. 13 and an end-systolic position shown in FIG. 14. The stroke volume, which represents the volume of blood pumped with each complete cycle, is 25 ml in this embodiment. This necessitates a relatively high heart rate and requires the entire design to incorporate specialized components to permit reliable operation for a very high number of cycles. The natural heart generally pumps approximately 60 to 200 beats per minute with the peak heart rate reduced to the range of 160 to 180 beats per minute beyond age 50. The cardiac output, which is the flow of blood pumped (generally expressed as liters per minute), is the product of the stroke volume multiplied by the heart rate. In normal adults, the stroke volume may vary from 30 to 40 ml up to 70 or 80 ml and can be in excess of 150 ml in large, conditioned individuals. Cardiac output in the range of 5 to 10 liters per minute is normal for conditions of rest to moderate exercise. With increasing exercise, the cardiac output may increase significantly. However, in patients suffering severe heart failure, cardiac outputs as low as 2 liters per minute may sustain their lives, and cardiac output of only 4 to 5 liters may permit a mobile quality of life.

The Devices and Technology Branch of the National Institutes of Health has specified that for left ventricular assist devices and total artificial hearts, systems must be capable of producing at least 8 liters per minute of flow with a heart rate below 120 beats per minute and a maximum filling pressure below 15 mm Hg. These criteria would be desirable and would more nearly duplicate the natural heart's function; however, such high output and low heart rate is by no means essential to maintain a good quality of life. Sufficient cardiac output can be obtained at higher heart rates with low stroke volume. This principle permits the blood pump to be sufficiently compact to be implanted in the ventricle, which has numerous advantages, as delineated above. With the maintenance of the efficient natural valve in the aortic position and the highly-efficient tissue valve in the mitral position, the blood pump of the present invention can achieve cardiac outputs of 7 liters per minute at heart rates of approximately 300 beats per minute. For conditions of rest, rates of 150 to 200 beats per minute provide outputs in the range of 3 to 5 liters per minute.

The design must provide the ability to undergo a very high number of flex cycles without failure. At an average of 250 beats per minute, the artificial heart must pump 130 million beats per year. The heart should be designed for 1 billion cycles which is approximately 7 to 8 years of operation. To achieve this very high number of flexing cycles, a multi-layer diaphragm of the roll-sock type is utilized. The diaphragm assembly 104 is composed of at least three layers, 132, 134 and 136, which are not adhered together in the regions where they flex and roll and are lubricated with graphite powder. These diaphragm layers are preferentially made of a polyurethane material such as BIOMER ®[2], which has been shown to have excellent mechanical properties in contact with human blood for almost two years of continual flexing. The rolling multi-layer diaphragm of the present invention will undergo more flex cycles without failure than the free diaphragm design utilized in the prior art. In the prior-art JARVIK 7 ® heart, diaphragms approximately seven thousandths of an inch thick for each layer, utilizing four layers with graphite lubricant between them, have flexed approximately 300 million cycles in real time in durability tests. A roll-sock diaphragm subjects the material to lower stresses and is expected to be several times more durable than the free diaphragm design.

[2] BIOMER ® is a registered trademark of Ethicon, Incorporated, Summerville, NJ.

In addition to the use of the multi-layer lubricated rolling diaphragm design, other elements of the system are designed for long-term durability, including use of heavy, well-lubricated bearings and use of a very smooth sinusiodal action of the mechanism which actuates the pusher-plate.

FIG. 20 illustrates the general mechanism utilized to accomplish this pumping action. Electric motors 174 and 176 provide power via their motor rotors 178 and 180 to a drive shaft 182 that is formed into a crankshaft at 186 and supports a bearing 114. As the crankshaft is rotated, it exerts a force via the ball bearing against the slot of a scotch yoke 112. This produces a sinusoidal push-pull action on the power shaft 110 that is fixed to the pusher-plate 108 that in turn is fixed to the diaphragm. The power shaft 110 is supported by a heavy ball bushing 118 supported by an extension 216 of the housing 144, and each end of the motor shaft/crankshaft assembly is supported by a heavy ball bearing 188 and 190. The mechanism is entirely contained within a hermetically-sealed, corrosion-resistant housing comprised of parts 144, 146 and 148 and utilizes a metal bellows 120 welded to the pusher-plate around its circumference at 220 and welded to the housing element 144 around its circumference at position 218. During assembly of the device, more welds are made around the circumference of the housing members at 157 and 158 to accomplish complete hermetic sealing. The power to the electric motors is provided by wires 160. The external cable 162 is connected to the internal wires by welded ceramic-to-metal feedthrough 164 of the type utilized with cardiac pacemakers. Thus the space within the assembly of pusher-plates, metal bellows, and housing generally indicated at 122 is a gas-filled chamber that varies in volume as the bellows moves between the end-systolic and end-diastolic positions. An inert gas such as nitrogen may be used to inhibit oxidation of the bearing lubricants, which will enhance their durability.

Referring to FIG. 13, the diaphragm 104 is pushed and pulled by the pusher-plate 108. The ring magnet 140 holds the diaphragm to the pusher-plate by attracting a magnetic stainless steel washer 138 embedded between the layers of the blood diaphragm assembly. The pusher-plate is connected to the main power shaft 110 by the threaded shaft 166. The main power shaft 110 is in turn connected to the scotch yoke 112 and is supported radially by the ball bushing 118. Rotation of the impeller shaft 110 is prevented by the welded spring bellows and the confinement of the scotch yoke section by bearing 114. As the electric motors rotate and drive the crankshaft 116, the counterbalances 200 to 202 rotate to maintain balance of the radial forces on the motor shaft. The chamber 124 enclosed between the diaphragm housing members 148 and 150 and the pusher-plate 108 is filled with hydraulic fluid. As the pump cycles between the systolic and diastolic position, the hydraulic fluid in this chamber moves in and out between the spaces of the bellows. The center of mass of the hydraulic fluid, which can be considered to be a somewhat donut-shaped body of fluid, moves back and forth along the axial direction of the main power shaft 110. The hydraulic fluid is preferentially a low viscosity inert fluid such as methyl silicone or a fluorocarbon fluid. These fluids are very stable and have an extremely low rate of diffusion through BIOMER ®. Diffusion of the fluid may be further reduced by providing a metalized surface film or other barrier layer on the hydraulic fluid-contacting portion of diaphragm 136. As the pusher-plate moves from its diastolic to its systolic position, blood is ejected from the ventricle. The overall density of the device is less in the end-systolic than in the end-diastolic position because the volume occupied by low density gas is increased as blood is ejected. Its center of gravity shifts back and forth axially during the cycle. The motion of the hydraulic fluid can be utilized to counterbalance this axial shift in center of gravity by selecting a fluorocarbon fluid with a higher density than the density of blood. Thus the entire system can be balanced well so that at a high heart rate it has little axial motion and exerts low thrust forces on the suture line.

During fabrication, the hydraulic fluid diaphragm 136 is glued to the tapered area of the pusher-plate in the region beneath the magnetic washer 138. Hydraulic fluid is then introduced into chamber 124 and the hydraulic fluid diaphragm is glued over the housing member 150 in the area of the retaining groove 151. The hydraulic fluid is maintained within the chamber by the O-ring seal 156 which was formed at a prior sub-assembly stage when housing member 150 was assembled into housing member 148. The O-ring seals 152 and 154 are not required in the final welded unit but are included in bench models, which are not welded together to allow disassembly for bench test evaluation.

Referring to FIG. 13, the stack of belleville washers in 168 is mounted under pre-loaded compression between the pusher-plate 108 and the housing member 144. This belleville washer stack acts as a nonlinear spring exerting force between the pusher-plate and housing along the axis of the main power shaft. Hardened steel inserts 170 and 172 retain and guide the stack of washers, which may undergo some sliding contact during the cycle of the heart. Thus the washers and hardened steel retaining elements are lubricated with an appropriate grease.

Referring to FIG. 14, assembly of the electric motors and shaft is best seen. Each electric motor is comprised of laminations and windings 174 and 176 and the motor rotors 178 and 180, which include permanent magnet elements. The motors may be commutated in a variety of ways including the use of hall effect sensors 206 and 212, mounted on printed circuit boards 208 and 214 in the vicinity of the ends of the motors, together with magnets 204 and 210 mounted on the motor rotors. Alternately, other types of sensing devices may be used to commutate the motor, or the back EMF method may be used, which requires no sensors mounted on the motor. In the back EMF method, the voltage and the current in the individual windings of the motor are monitored to provide the necessary timing information for commutation.

The shaft of each motor is held in a shaft bearing 188 and 190 supported within a portion of a housing member 142 and 192, which also holds the motor windings and the printed circuit boards. In this embodiment, the motor-retaining housings are separate parts that each contain a flange, 194 and 195, that are aligned with regard to one another by alignment pins 196 and are fastened together by screws 198. The motor housing sub-assembly is then fastened into the housing member 144 by bolts 199. Each motor shaft 182 and 184 is provided with eccentric counterbalances 200 and 202, and with crankshaft elements 116 and 186. During assembly, bearing 114 is mounted between crankshaft 116 and scotch yoke number 112, and then with proper alignment in an appropriate fixture, crankshaft member 186 is press-fitted into member 116. This assembly must be tight and perfectly aligned.

The embodiment of the invention shown in FIGS. 13 and 14 does not require a compliance chamber. The volume of gas within the housing and the metal bellows varies by 25 ml from the end-systolic to the end-diastolic position. The gas within the chamber is compressed and allowed to expand during the cycle. In other similar embodiments of the invention in which a compliance chamber such as the right ventricular pumping sac is used, the gas within the housing may be replaced with hydraulic fluid. In that situation, as the volume within the metal bellows and the volume within the chamber changes, the hydraulic fluid is alternately pumped into the right ventricular pump and then sucked back into the left intraventricular blood pump housing. In a device operated in such a fashion, the stack of belleville washers would not be necessary. Their function is to compensate for forces resulting from a reduced pressure within the housing when gas is used and for changes in the pressure during the operating cycle.

In order for the type of rolling diaphragm used with the present embodiment to function properly for an exceedingly high number of cycles, it must remain in the proper tightly-seated rolling position and must not stretch or invert. This is accomplished by using the proper relationship between the change in volume within the metal bellows, the volume of blood pumped by the pusher-plate, and the proper quantity of hydraulic fluid in the space between the bellows and the diaphragm. The principles that permit the correct relationship to be achieved are illustrated in FIGS. 15 and 16. Referring to FIGS. 15-A and 15-B, the metal bellows 224 is schematically represented enclosed within a cylinder 222. A diaphragm 226 separates a portion of the cylinder filled with hydraulic fluid 228 from another portion of the cylinder filled with blood 230. Above the cylinder, a second smaller cylinder 232 is mounted, connected to the larger cylinder by a small tube 234. The amount of blood for purposes of illustration is just sufficient to fill the larger cylinder. In FIG. 15-B, the metal bellows has been expanded by a mechanism which is not shown. The gas within the bellows is rarified and at a lower pressure in 15-B than in 15-A. The diaphragm 226 has moved to a position such that the volume of blood displaced out of the large cylinder and moved into the small cylinder 236 exactly corresponds to the increase in volume within the metal bellows. Thus the volume of blood within the cylinder 230 is diminished by the amount that the gas volume within the bellows is increased. The volume of hydraulic fluid 228 remains constant.

No matter what shape the diaphragm has, the volume of blood ejected from the large cylinder will exactly correspond to the increase in the volume within the metal bellows. This is illustrated in FIGS. 15-C and 15-D where a rolling diaphragm 238 is mounted on a supporting cup 240. The supporting cup is similar to a pusher-plate, but is not axially or radially supported, and it is not directly pushed by any mechanical connection to the bellows. It is, however, pushed hydraulically and may move from the position shown in FIG. 15-C to the position shown in FIG. 15-D, assuming that the supporting cup 240 is fixed to the rolling diaphragm approximately in the areas where it contacts the diaphragm in 15-C. The supporting cup 240 is free to tilt and move less axial distance if the diaphragm 238 partially inverts or to move radially out of alignment with the center of the cylinder. However, no matter what position it takes, the volume of blood ejected must still exactly equal the change in gas volume within the bellows. FIG. 15-E represents the embodiment of the invention illustrated in FIGS. 13 and 14. The rolling diaphragm 238 is mechanically pushed by the pusher-plate 242 that is directly attached to the bellows 224. The geometry and size relationships are such that throughout the stroke, the rolling diaphragm maintains a proper position and does not stretch, invert or kink. This proper relationship is represented in FIG. 16 where the volume of blood displaced by the pusher-plate as a percentage of the change in volume of gas within the bellows is plotted versus the distance moved by the pusher-plate as a percentage of full stroke. Line C represents a well-designed system where the actual relationships correspond very closely with the ideal relationship shown in line B.

FIG. 15-G illustrates the problems that arise if the pusher-plate 44 and rolling diaphragm are too small. The rolling diaphragm should have a shape as illustrated by the dotted line 246, but in the event the pusher-plate is too small, the rolling diaphragm will actually invert to the position shown by the solid line 248. This occurs because the volume of blood expelled from the large cylinder into the small cylinder 236 must equal the change in volume of the gas within the bellows. Since the hydraulic fluid does not change volume, if the pusher-plate is too small, the hydraulic fluid will force the diaphragm to invert to a shape such as shown by line 248. In FIG. 16, this is represented by line A, where, by the end of systole, that is, when the pusher-plate has moved 100% of its travel, the volume displaced by the pusher-plate is only 75% of the change in volume of the gas within the bellows.

FIG. 15-H illustrates the situation in the event that the pusher-plate 250 is too large. Again, since the volume of blood expelled from the cylinder 236 must equal the change in volume of the gas in the bellows, less blood must actually be expelled from the large cylinder than the pusher-plate and rolling diaphragm would tend to do. Therefore, provided that enough force is applied to the pusher-plate, the rolling diaphragm must stretch from the position indicated by the dotted lines 252 to the position indicated at the solid line 254, since the volume of hydraulic fluid is constant. This is illustrated in FIG. 16 by line D which shows that by the time full stroke of the pusher-plate has occurred, the volume replaced by the pusher-plate would tend to be approximately 125%. As drawn in FIG. 16, unless the diaphragm were able to stretch after the pusher-plate had reached approximately 75% of its full stroke distance, the system would lock up, and the pusher-plate would no longer be able to move without stretching the diaphragm. The relationships illustrated in FIGS. 15 and 16 show that only in the situation illustrated in FIGS. 15-E and 15-F will the rolling diaphragm have optimal support and the longest life expectancy. In the embodiment illustrated in FIGS. 13 and 14, this correct relationship is drawn to scale. The change in volume within the bellows is 25 ml and the stroke volume of the blood is also 25 ml for a pump with the inside diameter of the housing equal to 2.050 inches at the position shown by 221. Thus, the embodiment shown in FIGS. 13 and 14, in addition to illustrating the operative principles of the mechanism, demonstrates appropriate dimensional relationships of the various components in this example of one embodiment.

FIG. 15-I is an illustration of the hydraulically-activated intraventricular blood pump 258 to which the hydraulic fluid power is supplied by an actuator utilizing a variable volume bellows driven within a rigid housing 256. The pusher-plate 264 is shown to represent the approximate shape of an actual device in which part of the mechanism is nested below the pusher-plate. However, no rolling diaphragm is necessary within rigid chamber 256, and pusher-plate 264 could be flat or of any shape. The mechanism contained within the metal bellows pushes the bellows to the position indicated by the dotted lines 265. Hydraulic fluid is forced out of chamber 256 through tube 262 into the intraventricular blood pump 258. This forces the blood diaphragm within the intraventricular artificial heart to move from its end-diastolic position 260 to the end-systolic position indicated by the dotted lines at 261. The use of the metal gas-filled bellows together with a direct pusher-plate actuation or hydraulic fluid actuation provides a mechanism to power the artificial heart that does not require any compliance chamber other than that within the metal bellows itself.

The compression of the gas within the bellows at the end of the diastolic phase compared to the gas at the end of the systolic phase, provides an energy storage system and functions like a spring. When the gas is compressed, the energy is stored and when the gas expands, the energy is released. The pressure and force relationships involved must be appropriately balanced and matched to the mechanical capability of the motor and mechanism actuating the pusher-plate. FIG. 17 demonstrates how this can be accomplished. (Intraventricular artificial hearts can also function utilizing an air vent either to atmosphere or to a compliance chamber placed within the thorax, the abdominal cavity, or within the heart itself).

In FIGS. 17-A through D, the angular position of the motor and crankshaft of the artificial heart illustrated in FIGS. 13 and 14 is plotted against a number of parameters, including blood pressure and spring forces as well as the position of the pusher-plate. Referring to FIG. 17-A, pusher-plate displacement in inches is plotted as a function of the rotation of the motor. Between 0 and 180 degrees, the pusher-plate is moving from the end-systolic position illustrated in FIG. 13 by the dotted lines to the end-diastolic position illustrated in FIG. 13 by the solid lines. From 180 to 360 degrees, the pusher-plate is moving from the end-diastolic position to the end-systolic position. During the diastolic phase, (0 through 180 degrees), the pressure of the gas within the metal bellows and hermetically-sealed chamber 122 containing the motors and scotch yoke assembly increases from 390 mm Hg pressure to a peak of 524 mm Hg pressure. The volume of fluid labelled the fill/eject volume, (that volume of blood within the intraventricular artificial heart that constitutes a portion of the stroke volume), increases from 0 to 25 ml at the end of diastole. Thus the artificial heart is maximally filled with blood at the end of diastole. During systole, the gas pressure within the bellows diminishes from 524 mm Hg back to 390 mm Hg, returning the stored energy to the pusher-plate while the blood is being ejected from the pump.

This cycle occurs with each beat of the heart, and during one complete revolution of the motor, the displacement, fill/eject volume, and gas pressure undergo increases and decreases in a sinusoidal fashion determined by the geometry of the scotch yoke driving the pusher-plate. If a different mechanism such as a linkage or cam were utilized, these curves would not necessarily be sinusoidal. However the sinusoidal wave form has advantages for the smooth operation of a rotary mechanism at high speed.

FIG. 17-B illustrates the intraventricular blood pressure during diastole and systole in a hypothetical characteristic heart beat. Actual pressures in physiologic conditions will differ from this idealized wave form, which represents operating conditions under a relatively high systolic pressure load. It is most important to recognize that the amount of energy input into hemodynamic work to move the blood is practically zero during diastole and is significant during systole for the left intraventricular artificial heart. In applications where the device also actuates a right ventricular pumping mechanism, the hemodynamic work done during diastole will usually be about 20% of the work done during systole. Thus, matching of the spring and pressure forces involved can be optimized depending upon the specific application of the device in order to maximize overall energy efficiency of the system.

Figure 17A:
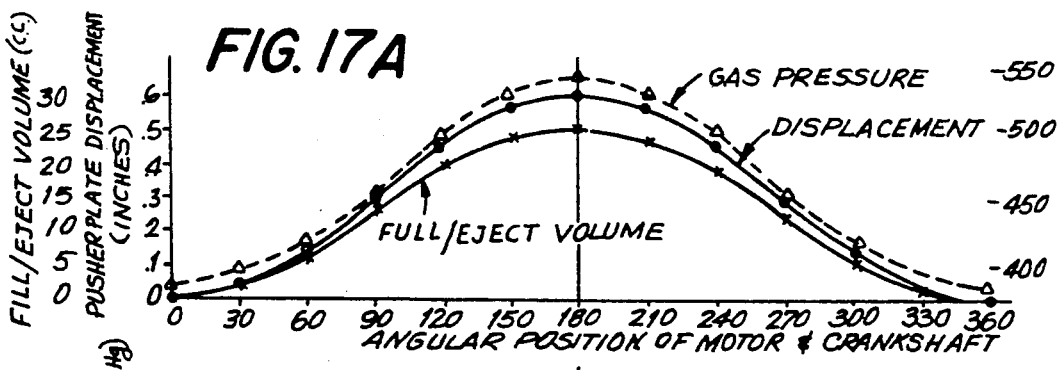
Figure 17B:
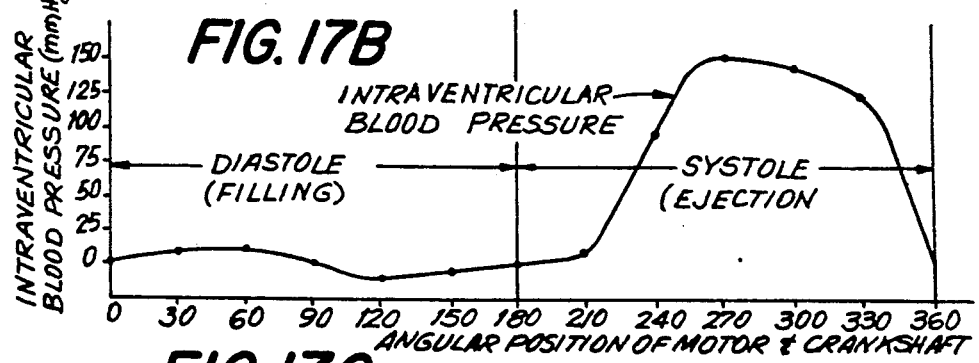
Figure 17C:
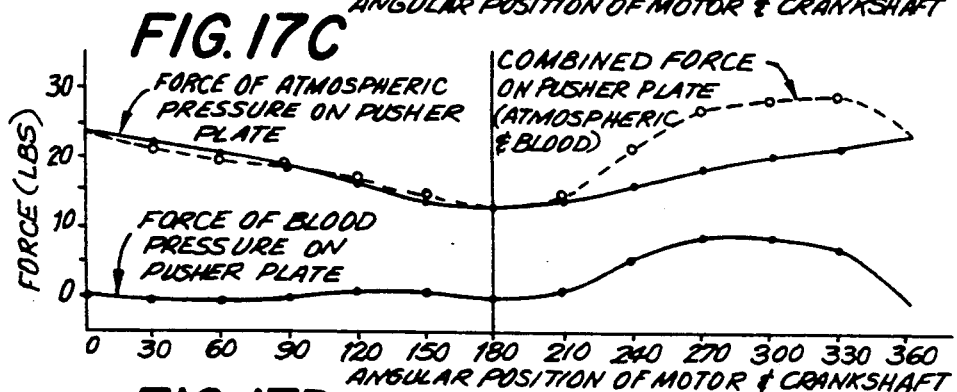
Figure 17D:
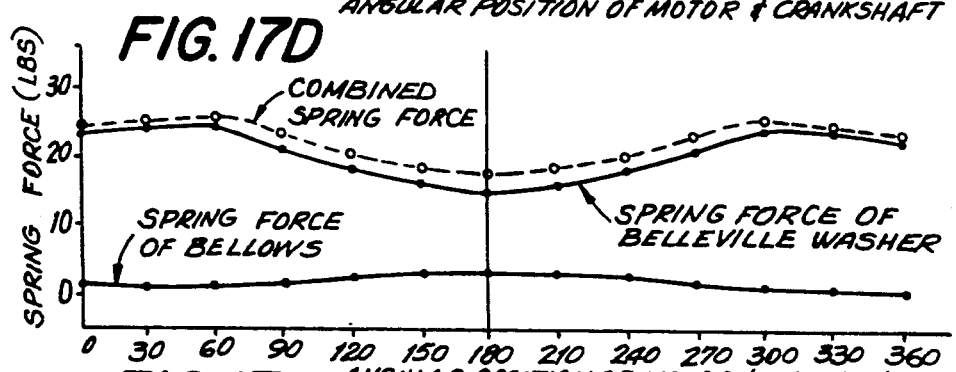
Figure 17E:
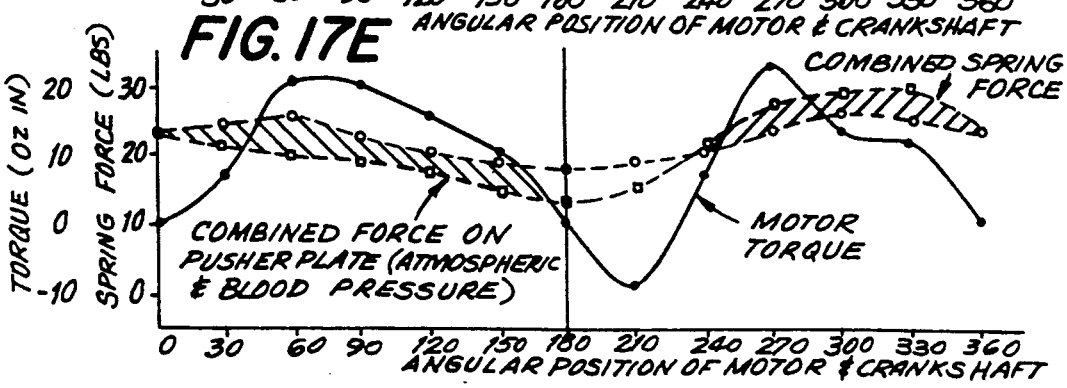

FIG. 17C shows the forces of the atmospheric pressure on the pusher-plate and the force of the blood pressure on the pusher-plate over the cycle. The gas pressure within the bellows is sub-atmospheric, in the range of 390 to 524 mm Hg compared with a usual atmospheric pressure of 760 mm Hg. Therefore, the higher external atmospheric pressure acting through the blood will tend to force the pusher plate from the end-systolic position towards the end-diastolic position. This force is greatest when the gas within the bellows is at the lowest pressure (end-systolic position), which in this embodiment is 23.7 pounds. At the end-diastolic position when the gas within the bellows has been compressed to its maximum extent the net force of the atmospheric pressure on the pusher-plate (the force that is not counter balanced by the gas pressure within the bellows) is diminished to 15.4 pounds. FIG. 17C also shows the force of the blood pressure on the pusher-plate which is seen to be low during diastole and increases to a peak value of 9.1 pounds during systole. The combined force on the pusher-plate by the atmospheric pressure and the blood is shown as the dotted line in FIG. 17C. This combined force always is exerted in the direction from the blood side towards the pusher-plate.

FIG. 17-D shows the forces exerted by the metal bellows and the stack of belleville washers within the mechanism. These two spring forces act in a direction opposite to the forces of the blood pressure and net atmospheric pressure and thus tend to reduce them. Note that the force of the spring bellows increases from 1 to 3 pounds during diastole and that the spring force of the belleville washers first increases from 23 to 23.5 pounds and then decreases to 15 pounds during diastole. During systole these spring forces change as shown in FIG. 17-D. The forces of the metal bellows and belleville washers are carefully selected by the design of these system components to yield the characteristics shown. The belleville washer stack is specifically chosen in this embodiment for its special spring characteristics that permit the force it exerts to be lower in the end-diastolic position than in the end-systolic position.

FIG. 21-C illustrates a belleville washer in the stack with its height, h, shown and its thickness, t, shown. FIG. 21-B illustrates the characteristic of belleville washers wherein the load varies as a percentage of the deflection of the height of the washer, depending upon the ratio of height to thickness. These curves are given for various ratios where $h=t$, $h=2t$, $h=2.83t$, and $h=3t$. We see that for washers of physical geometry where $h=3t$, the load (or force) first increases slightly from 40% to 50% deflection and then decreases markedly from 50% to 85% deflection. A spring of this type is used in the embodiment illustrated in FIG. 13. FIG. 21-C illustrates a stack of belleville washers in series. In this arrangement, the force exerted axially by the compressed stack is equal to the force exerted by each washer alone, but the displacement of the entire stack changes in an additive fashion by the displacement of each washer. Thus a stack in series can permit a long axial displacement while retaining the force characteristics of a single washer.

In the intraventricular artificial heart application, a very high number of operating cycles is required to obtain the necessary durability. This durability can be increased by utilizing a combined series and parallel stack as illustrated in FIG. 21-D. In this case, two belleville washers are placed one upon the other in a laminated fashion. Groups of these two-piece parallel stacks are then placed in series. The characteristics of this stack will be that the axial force exerted is equal to twice the force of a single washer, and the displacement of the entire stack will be equal to one half the displacement of the individual washers. Note that FIGS. 21-C and 21-D are drawn to scale to represent washers where $h=3t$ in both illustrations. Thus, the overall force-versus-displacement (load deflection) curve of the stacks illustrated in FIG. 21-C and 21-D will be the same. The area of contact of the stacked washers in 21-D is appropriately lubricated, and the washers are carefully quality-controlled for freedom from cracks and defects. If the washers are stress-relieved and have the right surface characteristics, such as results from shotpeening, the laminated stack shown in FIG. 21-D can achieve significantly higher durability in terms of the number of cycles than the non-laminated stack shown in FIG. 21-C. Additionally selecting the appropriate overall geometry of the washers to achieve the necessary spring forces and minimize the stress load within the material greatly enhances the reliability of the system.

Again returning to FIG. 17, the difference between the combined spring force and the combined force on the pusher-plate of the atmospheric and blood pressure represents the force that must be provided by the motor via the scotch yoke mechanism in order to move the pusher-plate and thus actuate the heart. In FIG. 17-E, these two curves are plotted, and the area between them is crosshatched showing the portions of the cycle where the motor must supply energy to move the pusher-plate. The motor torque required to provide this amount of force is also given in FIG. 17-E. Note that for part of the cycle between approximately 180 degrees and 230 degrees, the motor torque has a negative value. During this portion of the cycle, the net balance of forces is such that energy stored within the springs and relationships of atmospheric pressure to pressure within the bellows actually causes the pusher-plate to move and provide the energy to rotate the motor. If a very sophisticated electronic and battery system were utilized, the motor could function as a generator during this portion of the cycle and store energy electrically in the battery. In practical reality, this type of system is not necessary; however, the careful matching of system spring characteristics, gas pressure within the device, actuator (scotch yoke mechanism) characteristics, and motor speed torque characteristics yields a situation in which the motor load is generally evenly distributed between the diastolic and systolic phases. This reduces the peak motor torque required during maximum systolic blood pressure load and permits efficient operation of the motor. In other embodiments of the invention that utilize either a right ventricular pumping chamber or utilize a compliance sac or vent, the appropriate selection of spring forces in the bellows and the use or omission of the stack of belleville washers allows optimization of the system to minimize the torque requirements on the motor, thereby permitting reduced motor size and greater motor efficiency.

FIG. 27 is a longitudinal sectional view of a fluid-powered intraventricular artificial heart such as illustrated in FIG. 6, FIG. 11, and FIG. 12 with a power source to provide hydraulic fluid actuation. The blood pump is designed to permit implantation within the ventricular cavity of an average-sized adult male and provide a stroke volume of approximately 50 ml. The pump is round on cross-section, utilizes seamless multi-layer diaphragm construction, and is designed to have low stress at the junction of the blood diaphragm 284 to the housing 286 and attain long-term durability. Referring to FIG. 27, the blood pump utilizes a diaphragm having a spherical portion 290 and a portion which is the frustrum of a cone 288. The diaphragm is comprised of at least three layers, the blood diaphragm layer 284, the intermediate layer 294, and the hydraulic fluid diaphragm layer 292. The spaces between these layers are preferentially lubricated with graphite powder. The intermediate and hydraulic fluid diaphragm layers are bonded to a ventricle base 296 around their circumference at 310. They are also bonded to one another in this region, but throughout the rest of their surface (other than the area immediately adjacent to the outside of the base), the diaphragm layers are not bonded together. Hydraulic fluid diaphragm layer 292 is also bonded to a register band 308 during the molding process which permits the glued assembly of register band 308, hydraulic fluid diaphragm 292, and hydraulic fluid diaphragm 294. When the diaphragm assembly is in the end-diastolic position as shown in FIG. 27, the diaphragm assembly rests against a support screen 298, having holes 30 through which the hydraulic fluid may pass. The size and position of the support screen and the diaphragm layers are such that in the flexing position of the diaphragm 348, there is a fold of material that is not in contact with the base. This area represents the conical portion of the diaphragm, folded inward in the general fashion of a rolling diaphragm. Thus as the diaphragm moves from the end-systolic position 290, to the end-diastolic position shown in solid lines resting against screen 298 in FIG. 27, the diaphragm rolls evenly in the area of maximum bending, which is also the area of maximum stress upon the materials. This contributes to a long flex-life.

A length of the diaphragm between the position indicated by 346 and 344 is unadhered to the polymeric housing 286 and is fabricated this way using the mold assembly illustrated in FIG. 24. This permits the blood diaphragm to bend in the area of its contact to the housing at position 346 without high stresses associated with a sharp point of attachment such as point 384 shown in FIG. 25 for a prior art design.

With the blood pump of the present embodiment, the entire inner layer in contact with the blood is formed in one solution-cast layer without any seams where thrombus may form. A flexible polymer assembly consisting of the sewing ring segment 282, the connecting flange 316, the blood diaphragm 284, and the flexible housing 286, make up an integral unit which is soft and flexible and may be sutured in place within the natural ventricle, a technique thoroughly analogous to that described for the diaphragm sewing ring of the pusher-plate blood pump illustrated in FIG. 9-A. After this polymeric assembly is sutured in place within the heart, the rigid threaded connector ring 314 is placed in position over the connecting flange 316, and the snap-fit fasteners 318 are pushed through the holes in the threaded connector ring 314, shown at 322. String-like extensions of these snap-fit connectors 326 may be used to facilitate the assembly. After the threaded connector ring is positioned around the connector flange 316, it is prevented from rotating in respect of the sewing flange 282 and is essentially fixed by the suture line in one rotational position. The main housing support member 312 is then positioned between the threaded connector ring 314 and the flexible housing 286 and rotated to engage the threads of the connector ring 314 with its own threads. It is screwed in until it clamps the connecting flange 316 tightly. Thereafter snap-fit fasteners 320 (there may be four to eight such connectors around the circumference of the device) are pushed through holes 324 in the main housing support member or may be drawn through using string-like extensions 328. When this is completed, the blood is cleaned off the exposed surfaces of the blood diaphragm 284. The assembly, consisting of the base 296, the intermediate diaphragm, and hydraulic fluid diaphragm, is then screwed into the main housing support member until it reaches the fully-tightened position shown in FIG. 27. The space between the blood diaphragm and the other diaphragm layers indicated at 330 is vented to the outside through a channel 332 in the housing 286 that communicates with a ring-like air chamber 334 that is in turn in communication with a vent hole 336. A screw-in plug 342 that holds a resilient ball seal 340 to the threaded hole 338 is removed from the base and, using a small connector fitting with a tube and syringe (not shown), the excess air in the space 330 between the diaphragm layers is removed. The sealing ball 340 is placed to plug the hole, and the screw plug 342, is inserted and tightened. The hydraulic fluid chamber 302 is in communication with the conduit tube 62 that is held to the base 296 by threaded nut 304 that compresses the flange 202 of the tube against a tapered area on the base.

The design features and construction of this embodiment permit a generally cylindrical elongated seamless fluid-activated blood pump to be surgically implanted in the chamber of the left ventricle utilizing the above-described technique and assembly method.

FIG. 25 illustrates the method of fabrication of the blood diaphragm layer of the JARVIK 7 ® heart (prior art). In this design, the housing 378 is fabricated of BIOMER ® or another polyurethane material such as PELLATHANE ®[3]. The housing is quite stiff, but is slightly elastic and can be stretched over the hollow blood diaphragm mold 382. The housing is registered in position with relation to the diaphragm mold by a circumferential lip that fits within a groove 388 and has a contour that matches a step in the mold at 390. The dotted line 392 in FIG. 25 represents a design for a new fabrication method shown in FIG. 26 and is not representative of any structure in the JARVIK 7 ® heart. After the housing has been stretched over the hollow stainless steel diaphragm mold 382 and registered properly, liquid polyurethane solution is poured into the housing mold assembly through the valve rings and coats the entire inner surface of the mold housing assembly to form a continuous inner layer. The portion in contact with the stainless steel mold forms the blood diaphragm 380, and the remaining inner surface of the heart is coated with a blood-contacting layer 386 that adheres tightly to the housing and, in effect, becomes a part of it. Thus when the housing and blood diaphragm is removed from the stainless steel mold, the diaphragm is fixed to the housing circumferentially at point 384, which has a relatively sharp attachment geometry.

[3] PELLATHANE ® is a registered trademark of Upjohn, Incorporated, Kalamazoo, MI.

The blood diaphragm-housing assembly is placed over a base with a multi-layer diaphragm designed such that during full pressurization of the JARVIK 7 ® heart by compressed air at the end-systolic position, there is very little stress on the blood housing-diaphragm attachment point 384. Thus the JARVIK 7 ® heart diaphragm is able to flex for several hundred million cycles without breaking. However, eventually the air diaphragms of the JARVIK 7 ® heart experience creep under the forces of the compressed air pressure and stretch in such a manner that they exert tension on point 384 at the end-systolic portion of each cardiac cycle. Eventually the diaphragm fails at point 384 which constitutes the limiting factor of the durability of the entire design.

A new artificial heart structural component design in this critical region and the fabrication method illustrated in FIG. 26 prevents this failure from occurring. If the blood diaphragm layer 380 continues in the region indicated by the number 385 without attachment to the housing 378, the high stress from the air diaphragms will not occur at point 384, and the life of the ventricle will be greatly extended. To achieve this geometry, a different housing shape and mold shape is used as illustrated in FIG. 26. The housing 394 is fabricated with a thin section 398 and otherwise would have the same form as if the housing 378 were cut off at the dotted line indicated as 392. The thinned portion of the housing is flexible enough to stretch over the outwardly-tapered portion of the stainless steel blood diaphragm mold 396 indicated at 400. A registry groove in the mold 401 receives a correspondingly-shaped circumferential lip of the diaphragm to hold it in proper position with respect to the mold. The circumferential separator section of the mold 406 makes tapered contact with the housing at 408. Liquid polyurethane solution poured into the assembly of the stainless steel mold and housing coats the inner surfaces and forms both the blood diaphragm 404 and an inner coating on the housing. Circumferentially, in the area indicated at 410, the blood diaphragm is not attached to the housing, and after the blood diaphragm-housing assembly is removed from the stainless steel mold 396, it takes the same form as the housing prior to stretching it over the tapered mold and fits properly against the base assembly. Thus the result obtained is a geometry equivalent to that which would have been obtained if the diaphragm mold 396 had the contour indicated by the dotted lines 402 instead of its actual outer contour 400 and the polyurethane solution did not stick to the inside of the housing in the area indicated by number 410.

FIG. 24 illustrates a similar method of fabrication utilized with the intraventricular blood pump of the configuration illustrated in FIG. 27. The polymer portion of the housing, which, without stretching, would lie in the position shown by the dotted lines at 368, is stretched over the stainless steel blood diaphragm mold and lies in the position shown at 370. This is analogous to the stretching of the thin housing member over the mold illustrated in FIG. 26. Mold support members 352 and 354 retain the flange 316 in place and are bolted together by a series of bolts 362 located around the circumference of the mold assembly. The outer tip of the sewing ring is also held in place by a clamping ring 356 and by a number of screws 364. With mold members 352, 354, and 356 clamped to the sewing ring housing assembly, and with portion 370 of the housing stretched over the diaphragm mold 350, the housing can be clamped tightly by bolts 360 using spacer rings 358 to ensure the proper position. With the sewing cuff 282, connecting flange 316, and housing 286 thus held in the mold assembly, liquid polyurethane solution is then poured into the mold to coat the inner surface and form the blood diaphragm and a coating layer over part of the housing and sewing cuff. The blood diaphragm has a section that is a portion of a sphere 374, a section that is a frustrum of a cone 372, and a radius 375. It is attached to the housing at point 344. After this solution-cast diaphragm and lining is dried and cured, the mold is disassembled, and the polymeric parts removed. The stretched housing 370, returns to its original form as indicated by the dotted lines 368. A portion of blood diaphragm 345 lies against the housing without being adherent to it. The proper geometry has been achieved.

Other embodiments of intraventricular artificial hearts may utilize rotary blood pumps. These may be of several varieties, including axial-flow pumps, mixed-flow pumps, and centrifugal-flow pumps. A centrifugal-type intraventricular blood pump is illustrated in FIG. 5, and the preferred embodiment of this is detailed in FIGS. 18 and 28. FIG. 18 is a three-dimensional view showing the rotating part of the pump, which consists of the motor rotor 412 and impeller assembly 462, attached to the motor rotor by support pins 420. This rotating member is supported radially by a bearing that is comprised of a wire 436 maintained in tension. The wire is preferentially ground to very precise dimensions with a smooth polished surface finish. The material should be a very high strength non-corrosive alloy, such as Stellite 25.

Referring to FIG. 28, the rotor 412 contains the magnets 424 of a brushless DC motor with the windings 482 located within the housing of the pump 446. Blood flows through channel 476, which in normal motor terminology is called the "air gap" of the motor. Thus, via the electric motor, the rotor assembly carrying the pump impeller is magnetically driven within the bloodstream. The rotor is comprised of housing members 426 and 428 welded circumferentially at points 430 and 432 so as to completely hermetically seal the motor magnets and prevent blood contact with the magnet material. The rotor contains a generally cylindrical bushing 434 made of a hard material such as ceramic, pyrolitic carbon, or a synthetic crystal such as sapphire. This bushing has an axial hole through which the bearing wire 436 passes. The gap between the wire and the bushing is extremely narrow and is filled with blood plasma. There is very little room for thrombus to form in this crevice since the bearing wire 436 might typically be 0.030 inches in diameter, and the gap might be only 0.0002 inches. The bearing wire 436 is maintained in a rigid state of tension by a spring 442 that acts between a washer 454 and a support hub 438, held against a tapered area of the housing 448 on the tips of the blades 444, which closely match the housing taper at 446. The bearing wire 436 has a tapered, widened portion 450 that locks into the support hub 438. At the other end of the wire, a ball 452 is welded in place after the pump is assembled to permit spring tension to be transmitted axially to the wire. The support hub 438 is fitted with an axial bearing 458, which is also made of a ceramic or jewelled material and can contact bushing 434 if the impeller is displaced axially. Similarly, at the other end of the rotor, another axial thrust-bearing member 436 is located, also comprised of a similar material that is capable of acting as a bearing for thrust loads in the opposite direction. In usual operation, the bushing 434 should not contact either the thrust members 456 or 458. The small gap 470 is maintained at one end of the rotor, and another small gap 472 is maintained at the opposite end.

During rotation and centrifugal pumping, the axial thrust-load on the impeller and rotor is small. The rotor includes a ring magnet 460 that is positioned between two other ring magnets 466 and 468, axially aligned within the housing. These three magnets are arranged with their polarity such that the ring magnet on the motor is opposed by repulsion of the magnetic fields of the stationary magnets in the housing, which resist forces tending to move it axially in either direction. Thus, the complete bearing system of this embodiment includes a radial journal bearing having as its shaft a small diameter wire in tension, and an axial thrust-bearing assembly comprised of appropriately-aligned ring magnets with opposing poles. Mechanical thrust-bearing surfaces are also provided to prevent the rotor from hitting the housing in the event of sudden forces, such as shock or vibration, which might move the rotor assembly axially despite the magnetic thrust bearings. The blood flow path around the support hub 438 is such that the exposed portion of the bearing wire 436 in gap 470 is washed by a high blood flow, and this prevents thrombus formation. A similar geometry is utilized at the other end of the rotor to assure that the exposed portion of the bearing wire 436 is also well washed in the gap 472 by high blood flow, which prevents thrombus formation. The rotor assembly includes an inner member 464 that carries impeller blades, one of which is indicated at 418. This impeller member is fixed to the motor rotor by three pins, one of which is shown at 422 that pass through support pins 420. The outer member of the pumping impeller 462 also carries impeller blades, one of which is indicated at 416, and the two members are welded together after insertion of the support pins 422 and insertion of the ring magnet 460. This completes the rotor assembly.

The housing is similarly comprised of several parts 440, 445, 447, and 448 that are welded together circumferentially at positions 486, 488, and 490 after the pump is assembled.

The centrifugal-type intraventricular blood pump is implanted by suturing in a flexible sewing cuff 38 after the leaflets of the aortic valve have been sutured shut. This is shown in FIG. 5. The sewing cuff 38 is then attached to the housing of the blood pump by means of a nut 52 that captures a flange 492 of the sewing ring. The end of the housing is tapered where it seats against the flange 492, and this permits it to align and seat properly so that only a very small gap is present at position 434.

Blood entering the inflow passes around the rotating hub as shown by the arrows 474. Blood flows through the "air gap" of the motor, and when it reaches approximately position 478, the stream is divided into two channels of equal area. This is indicated by the arrows leading from point 478. If the blood takes the outer channel, it will pass on one side of the impeller assembly, and if it takes the inner channel, it will wash across the bearing wire gap 472 and then pass to the other side of the impeller. As the flow moves radially along the impeller, it is given a rotational push by the impeller and its blades, which increases the rotational velocity of the fluid and correspondingly increases the fluid momentum. By the time the fluid reaches the outer circumferential channel 480 around the outside diameter of the impeller assembly 414, its rotational momentum is greatly increased. The diffuser 40 is a tapered tube designed to convert the rotary fluid momentum into flow and pressure energy at the outflow. The diffuser section 40 leads to the outflow graft 42 that is anastomosed to the ascending aorta.

A centrifugal intraventricular blood pump may be operated at a continuous rotational speed to deliver a generally pulseless flow to the arterial system. Alternatively, the speed of rotation of the impeller may be cyclically increased and decreased by a control system to provide pulsations in the arterial pressure. The type of blading used with the pump impeller may be varied depending upon the flow and pressure desired. Centrifugal pump impeller systems utilizing a series of concentric cones or a series of generally parallel discs may be used rather than impellers with blades to reduce the blood damage for long-term use. With proper impeller design, flows of 5 to 10 liters per minute against an arterial blood pressure of 100 to 150 millimeters of mercury are achieved at rotational speeds of 2,000 to 4,000 rpm with a pump impeller having an outside diameter of approximately 4.5 cm.

Another embodiment of a rotary intraventricular blood pump is show in FIGS. 11, 19, and 29. FIG. 19 shows the rotor of the intraventricular axial flow pump suspended radially on a bearing system using a wire in tension 506 very similar to the bearing system used with the centrifugal pump embodiment. The motor rotor is similarly encased in the rotor 500, which carries the rotor blades 502 of the axial flow pump. The stator blades of the axial flow pump 510 are supported on a stationary hub 508. Referring to FIG. 29, the detailed assembly of the preferred embodiment axial flow pump is shown. The motor magnets 504 and a bar magnet 520 that comprises part of the magnetic thrust-bearing system are encased in the rotor housing by welding in a similar fashion to that described for the centrifugal embodiment of the invention. The axial flow pump impeller blades 502 are located on the outflow side of the rotor and have a small hub diameter with a tip diameter approximately the same as the outer diameter of the rotor. The gap between the tip of the impeller blades 502 and the housing 514 is typically less than 1 mm. The tip diameter of the blades may be approximately 14 mm, and the hub diameter may be approximately 7 mm. With proper impeller blading design, the pump may be operated at speeds in the range of 5,000 to 7,000 rpm to obtain blood flows of 5 to 10 liters per minute against an arterial pressure of 100 to 150 mm Hg with an acceptable level of blood damage. The hub 508 supports outflow stators 510 that fit against a tapered section 512 of the housing 514. Thus, when axial tension is exerted against the bearing wire 506 by the spring 518 acting against the washer 540, the tips of the finely-machined outflow blades nest tightly into the tapered bore of the housing and seal the gap. The bearing system of the axial flow pump intraventricular artificial heart incorporates ceramic or jewelled matching members 526, 528, and 530 that may act as thrust bearings as well as rotary bearings if the fluid forces close either gap 564 or gap 568 and move the rotor 500 out of its central position. However, the design includes magnetic thrust-bearings through the action of opposing magnetic poles between rotor magnet 520 and stationary magnets 522 and 524. The blood flow path within the axial flow pump is arranged to thoroughly wash the gap at each end of the rotor and prevent thrombus formation around the wire in the area of the gap at 564 and 568.

Blood enters through the inflow sewing flange 546 as indicated by the arrow 560. Next, the blood flows through the inflow graft 70 and passes through the connector tube 544 that reduces the diameter of the flow stream and increases the velocity of the flow reaching point 562. This better washes the end of the rotor. The flow then passes around the rotor and, as indicated at 566, flows through the "air gap" between the motor windings at 532 and the motor magnets 504. The diameter of the flow path is then reduced as the blood crosses the impeller, which imparts rotational energy to the fluid, increases its radial momentum, and propels the blood against the outflow stator set 510. These outflow stators convert the rotational energy of the fluid momentum into axial flow and pressure as the fluid exits the pump 570 through the outflow graft 72.

Electric power is supplied to the motor via the power cable 80 which is encapsulated at 538 in the area where the wires are brought through the housing. Hermetic feedthroughs 536 are used to bring the wires into the motor and assure a seal that will not permit corrosive blood to enter the motor. The hermetic sealing of the motor compartment is accomplished by welding at seams 534 and 535 in the course of assembly of the system. The end cap 542 may also be welded to part of the housing 516. The axial flow pump, which is generally cylindrical, may be encased in a polymer body 78 to make the pump better conform to the shape of the intraventricular chamber. Additionally, in this embodiment, as in all other embodiments, the outside surface of the intraventricular blood pump may be covered with a porous fabric or other porous surface to permit good tissue ingrowth and help prevent infection.

Surgical implantation of the axial flow pump intraventricular artificial heart is accomplished using both inflow and outflow grafts that are first sutured into the natural heart and then connected to the artificial heart. Both these connectors utilize connector nuts 552 and 558 and polymeric connector flanges 550 and 556 configured to be properly aligned on a tapered portion of the housing on which the connection is made and held there in compression by the nut.

Embodiments of intraventricular blood pumps that are powered by electrically stimulated muscle grafts are shown in FIGS. 30 through 35. In FIG. 31, an intraventricular blood pump blood sac is sutured into the ventricular cavity near the mitral and aortic valves at suture line 586. This procedure is similar to those indicated for intraventricular blood pump designs and utilizes a prosthetic mitral tissue valve while preserving the natural aortic valve. The muscle graft 588 that powers the intraventricular pump may be a translocated muscle from the patient's own body or may be a transplanted muscle from another individual. FIG. 31 shows the way in which this muscle is positioned within the enlarged natural left ventricle 590 and anchored by sutures 592 and a large felt support pad 580. The blood sac itself 584 in FIG. 30-A generally has the shape of the natural ventricular chamber. It is soft and flexible and may be rolled up to permit suturing of the sewing cuff 574. A wire embedded near the area of the sewing ring supports the sac and prevents it from being distorted out of round in the area of the suture line. The outer wall 572 may be of non-uniform thickness and may contain thinner sections 584 and thicker rib like sections 582. Near the tip of the sac, a suturing tongue 578 is provided to permit the tip of the sac to be anchored via sutures to the apex of the heart utilizing the apical felt support pad 580. The ribbing of 582 helps control the folding pattern when the muscle graft contracts. Additionally the ribbing provides a "memory," resiliently tending to open towards the full position shown in 30-C. Thus, as the muscle contracts, the chamber undergoes a controlled folding pattern as illustrated in 30-D.

In some cases, where the natural ventricle is not sufficiently enlarged by heart failure to permit implantation of the entire muscle graft within it, a portion of the left ventricular wall may be cut away and replaced with transplanted or repositioned muscle. FIG. 32 shows this situation in which the ventricular septum 602 is left intact, and a replacement left ventricular wall 594 is sutured to the natural heart at 598 and 600. An internal layer of muscle 596 is analogous to the muscle 588 implanted within the natural ventricular cavity in FIG. 31. In this case, the tip of the blood sac is also anchored to an apical felt support pad 580 by sutures 604.

The muscle-powered intraventricular blood pump of the sac-type illustrated in FIGS. 31 and 32 has some disadvantages because the folding of the sac is not precisely controlled, and the contraction of the muscle may cause the sac walls to rub together and damage the blood. Without a well-controlled folding pattern the contracting muscle may cause stress concentration on the sac, which can result in relatively early failure. The embodiment illustrated in FIGS. 33, 34, and 35 illustrates a preferred embodiment of an intraventricular artificial heart powered by stimulated muscle grafts. FIG. 33-A shows a longitudinal section of a blood sac 614 having a sewing cuff 612, an attachment flange 622, snap-fit fasteners 624, and a metallic hermetic stainless steel washer 636 implanted within the blood sac at its apical end. This blood sac may first be sutured into the natural heart using sutures 648 to form the suture line 650, which may be supported by pledgets 662 in a manner similar to that described for previous embodiments of the invention. In this case, the prosthetic mitral valve 652 used is preferentially a tissue valve. The device incorporates an inner hydraulic fluid sac 630 and an outer housing 616 that are joined together to enclose a hydraulic fluid chamber 632. The inner and outer hydraulic fluid sacs 616 and 630 are glued over a connector ring 618 in the vicinity of the connector flange of the blood sac 622.

During surgical connection, the connector ring 618 is screwed into the nut 620 to clamp the retaining flange 622, the outer hydraulic fluid sac 616, and the inner hydraulic fluid sac 630 together. The outer hydraulic fluid sac has three thickened areas or ribs 626 that contain support wires 628 embedded therein. These support wires are continuous wire rings that are bent into the appropriate geometric form well indicated in FIG. 35. In this embodiment, the longitudinal ribs 626 are wire-reinforced and relatively stiff. The device is implanted such that as a surrounding muscle graft contracts and squeezes against it, the hydraulic fluid chambers and blood chambers change in geometry is as shown in FIG. 33-B to 33-C. Both the blood sac and inner hydraulic fluid sac fold uniformly in a trilobed pattern and are protected from being creased or crushed together by the relatively rigid ribs 626. The outer hydraulic fluid chamber 616 may be covered with a porous fabric or other porous surface to permit tissue ingrowth. The wall of the outer housing is varied in thickness as indicated in FIGS. 33-B and is molded into the configuration shown in FIG. 33-B such that the resilient memory of the material provides a restoring force to increase the blood volume within the pump to aid filling. The assembly is separable into four pieces as shown in FIGS. 33 and 35. These are the blood sac 614, the hydraulic fluid sac and outer housing with the attached connector ring 616, the nut 618, and the end cap 646, which contains a permanent magnet 640 and an O-ring seal 644.

During implantation, after the blood sac 614 is sutured in place, the nut 620 is positioned over the flange indicated by arrows 664 and attached with snap-on fasteners 624. The hydraulic fluid sac and connector ring assembly is then placed over the blood sac. At this point in the assembly, the end cap 646 is not in place, and air trapped between the blood sac and the inner hydraulic fluid sac may be withdrawn with a syringe and a small tube through the hole in the device shown at 634. As the connector ring and hydraulic fluid sacs are rotated and tightened against the nut, the air trapped between the blood sac and inner hydraulic fluid sac is withdrawn. Finally, the end cap is screwed into place against member 642, which positions the magnet 640 in the appropriate location to attract the metal washer 636 implanted at the tip of the blood sac and help maintain the blood sac in proper place.

FIG. 34 illustrates a muscle-powered intraventricular artificial heart utilizing the surgical technique in which part of the left ventricular muscle wall is replaced by a muscle graft 654 sutured to the remnant of the natural heart at position 658 and 660. The muscle graft may use several layers indicated by the dotted lines 656, which may result from wrapping a relatively flat elongated muscle around the prosthetic device.

The principles of operation described in these embodiments of intraventricular blood pumps and the methods of surgical implantation are intended to be illustrative of the practice of the present invention. Without departing from the principles of operation of the present invention, other embodiments and variations of the surgical method can be utilized. Thus, the information disclosed in the description of the present invention is intended to be representative of the principles that I have described. It will thus be seen that the objects of the invention set forth above and those made apparent from the proceeding description are efficiently attained and as certain changes may be made in the above articles and constructions without departing from the scope of the invention, it is intended that all matter contained in the above description or shown in the accompanying drawings shall be interpreted as illustrative, but not in a limiting sense. It is also to be understood that the following claims are intended to cover all of the generic and specific features of the invention herein described and all statements of the scope of the invention which, as a matter of language, might be said to fall therebetween.

What is claimed is:

1. A method of surgical implantation of at least one prosthetic blood pump within the heart comprised of:
    creating surgical access via surgical incisions to at least one of the four chambers of the heart such that the major coronary arteries are preserved;
    suturing via suture lines one or more connectors to permit attachment of the blood pump within the heart; testing the suture lines and repairing any leaks; securely attaching the blood pump to the connectors; removing any air trapped within the blood pump; initiating pumping;
    repairing the surgical incisions.

2. The method of surgical implantation of prosthetic blood pumps within the heart described in claim 1 in which the size of one or more chambers of the heart into which the components of the artificial heart system are implanted is enlarged using a muscle graft or split-thickness flap of cardiac muscle tissue.

3. The method of surgical implantation of at least one prosthetic blood pump within the heart as described in claim 1 in which inflow anastomosis is made within the heart, and outflow anastomosis is made outside the heart to either the aorta or the pulmonary artery.

4. The method of surgically implanting an intraventricular artificial heart comprising:
    excising the natural heart from the patient;
    suturing the intraventricular artificial heart and any requisite prosthetic valves within said excised natural heart;
    reimplanting the natural heart together with the intraventricular artificial heart into the patient.

5. A method of treating heart disease by supporting the pumping function of the heart of a patient in need thereof comprising implanting an electric motor together with other components of a blood pumping device into the natural heart of said patient and applying electric energy to the motor from a source outside the heart to pump all or part of the blood flow required to sustain the life of the patient.

6. The method of treating heart disease by supporting the pumping function of the heart of a patient in need thereof as described in claim 5 in which the outflow of the blood pumping device is channelled into the aorta of the patient's heart at a position distal to the natural aortic valve or into the pulmonary artery at a position distal to the natural pulmonic valve.

7. A method of treating heart disease by supporting the pumping function of the heart of a patient in need thereof via major surgery by implanting a rotary blood pumping device into one or more of the ventricles or atria of the natural heart of said patient, and applying energy to the device from a source outside the heart to pump all or part of the blood flow required to sustain the life of the patient.

8. The method of treating heart disease by supporting the pumping function of the heart of a patient in need thereof as described in claim 7 in which the outflow of the blood pumping device is channelled into the aorta of the patient's heart at a position distal to the natural aortic valve or into the pulmonary artery at a position distal to the natural pulmonic valve.

* * * * *